United States Patent
Eastham et al.

(10) Patent No.: US 11,981,951 B2
(45) Date of Patent: May 14, 2024

(54) PROCESS FOR THE PRODUCTION OF METHYL METHACRYLATE

(71) Applicant: Mitsubishi Chemical UK Limited, Billingham (GB)

(72) Inventors: Graham Ronald Eastham, Redcar (GB); Zoe Bethany Clare Disley, Nottingham (GB); David William Johnson, Redcar (GB); Gill Stephens, Nottingham (GB); Mark Waugh, Redcar (GB)

(73) Assignee: Mitsubishi Chemical UK Limited, Billingham (GB)

( * ) Notice: Subject to any disclaimer, the term of this patent is extended or adjusted under 35 U.S.C. 154(b) by 490 days.

(21) Appl. No.: 16/463,089

(22) PCT Filed: Nov. 22, 2017

(86) PCT No.: PCT/GB2017/053500
§ 371 (c)(1),
(2) Date: May 22, 2019

(87) PCT Pub. No.: WO2018/096326
PCT Pub. Date: May 31, 2018

(65) Prior Publication Data
US 2019/0284587 A1  Sep. 19, 2019

(30) Foreign Application Priority Data
Nov. 23, 2016  (GB) ...................... 1619827

(51) Int. Cl.
C12P 7/62 (2022.01)
C12N 9/00 (2006.01)
C12N 9/02 (2006.01)

(52) U.S. Cl.
CPC ............ C12P 7/62 (2013.01); C12N 9/00 (2013.01); C12N 9/0008 (2013.01); C12N 9/001 (2013.01); C12Y 102/04004 (2013.01); C12Y 103/03006 (2013.01)

(58) Field of Classification Search
CPC ... C12P 7/14; C12P 7/62; C07C 67/02; C07C 57/04; C12N 9/00; C12N 9/0008; C12N 9/001; C12Y 102/04004; C12Y 103/03006; C12Y 108/01004; C12Y 203/01168
See application file for complete search history.

(56) References Cited

U.S. PATENT DOCUMENTS

| | | | | |
|---|---|---|---|---|
| 2003/0077340 A1* | 4/2003 | Rao | ...................... | C12P 7/6472 424/727 |
| 2006/0003332 A1* | 1/2006 | Hyldig-Nielsen | ..... | C07K 14/31 435/6.1 |
| 2010/0021977 A1* | 1/2010 | May | ........................ | C12P 13/02 435/135 |
| 2010/0204509 A1* | 8/2010 | Protzmann | ............... | C07C 67/03 560/217 |
| 2011/0245521 A1* | 10/2011 | Fassbender | ............. | C11C 3/003 554/154 |
| 2013/0065279 A1* | 3/2013 | Burk | ......................... | C12P 7/62 435/88 |
| 2013/0172598 A1* | 7/2013 | Knebel | .................... | C07C 67/03 560/204 |
| 2015/0184207 A1* | 7/2015 | Sato | ................ | C12Y 203/01084 435/135 |
| 2018/0171368 A1* | 6/2018 | Eastham | ......... | C12Y 103/03006 |

FOREIGN PATENT DOCUMENTS

| | | |
|---|---|---|
| EP | 2894224 A1 | 7/2015 |
| EP | 3115460 A1 | 1/2017 |
| IL | 90820 A | 3/1993 |
| JP | 56077242 A | 6/1981 |
| JP | S57134500 A | 8/1982 |
| JP | S57183799 A | 11/1982 |
| JP | S5835197 A | 3/1983 |
| JP | S5867699 A | 4/1983 |
| JP | S5877895 A | 5/1983 |

(Continued)

OTHER PUBLICATIONS

Lin et al. (1999) Prediction of Octanol-Water Partition Coefficients Using a GroupContribution Solvation Model, Ind. Eng. Chem. Res., vol. 38, pp. 4081-4091.*
Neveu et al. (2012) Lubricant and Fuel Additives Based on Polyalkylmethacrylates , Elsevier B.V. publish, pp. 453-476.*
Brenda (2021 update) Information on EC 1.3.8.1-short-chain acyl-CoA dehydrogenase, p. 1.*
Petrochemical Blog (2018) N-Butyl Methacrylate: a Plasticizing Methacrylate Monomer, pages.*

(Continued)

Primary Examiner — Iqbal H Chowdhury
(74) Attorney, Agent, or Firm — Shumaker, Loop & Kendrick, LLP

(57) ABSTRACT

The present invention relates to a process for the production of methyl methacrylate. The process of the present invention comprises the steps of: a) providing a microorganism in a fermentation medium, under conditions which said microorganism will produce a $C_3$-$C_{12}$ methacrylate ester; b) providing an organic phase in contact with the fermentation medium, said organic phase including $C_3$-$C_{12}$ methacrylate ester in a higher concentration than that in the fermentation medium; c) removing organic phase containing the said $C_3$-$C_{12}$ methacrylate ester from contact with the fermentation medium; and d) transesterifying the removed $C_3$-$C_{12}$ methacrylate ester with methanol, optionally after separation from the organic phase, to produce methyl methacrylate.

33 Claims, 7 Drawing Sheets
Specification includes a Sequence Listing.

(56) References Cited

FOREIGN PATENT DOCUMENTS

| | | |
|---|---|---|
| JP | S58192900 A | 11/1983 |
| JP | 2000262288 A | 9/2000 |
| WO | 1999003988 A1 | 1/1999 |
| WO | 2000018935 A1 | 4/2000 |
| WO | 2005010175 A1 | 2/2005 |
| WO | 2005059093 A2 | 6/2005 |
| WO | 2006028063 A1 | 3/2006 |
| WO | 2014/096850 A1 | 6/2014 |
| WO | 2014096850 A1 | 6/2014 |
| WO | WO 2015022496 A2 * | 2/2015 |
| WO | WO-2015022496 A2 * | 2/2015 ................ C12P 7/62 |
| WO | 2016185211 A1 | 11/2016 |

OTHER PUBLICATIONS

HMDB (2005) Showing metabocard for alpha-Ketoisovaleric acid, pp. 1-33.*

MyBioSourec (2005) Acyl-coenzyme A oxidase, pp. 1-6.*

Hoffmeister et al., "Mitochondrial trans-2-Enoyl-CoA Reductase of Wax Ester Fermentation from Euglena gracilis Defines a New Family of Enzymes Involved in Lipid Synthesis", The Journal of Biological Chemistry, vol. 280, No. 6, Feb. 11, 2005, pp. 4329-4338.

Datsenko et al., "One-step inactivation of chromosomal genes in *Escherichia coli* K-12 using PCR Products", Proceedings of National Academy of Sciences, vol. 97, No. 12, Jun. 6, 2000, pp. 6640-6645.

Cho et al., "Interactions between Integrase and Excisionase in the Phage Lambda Excisive Nucleoprotein Complex", Journal of Bacteriology, vol. 184, No. 18, Sep. 2002, pp. 5200-5203.

International Search Report (ISR) for PCT/GB2017/053500 dated Jan. 11, 2018 (5 pages).

Written Opinion of the International Searching Authority for PCT/GB2017/053500 dated Jan. 11, 2018 (8 pgs.).

International Preliminary Report on Patentability (IPRP) for PCT/GB2017/053500 dated May 28, 2019 (9 pages).

Search Report for GB 1619827.7 dated Aug. 10, 2017 (3 pages).

English translation of Office Action for JP 2019-547793 dated Jun. 29, 2021 (2 pages).

* cited by examiner

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: primer sequence

<400> SEQUENCE: 1
ggcctgtcat gagtgattac gagccg                              26

<210> SEQ ID NO 2
<211> LENGTH: 32
<212> TYPE: DNA
<213> ORGANISM: Artificial Sequence
<220> FEATURE:
<223> OTHER INFORMATION: primer sequence

<400> SEQUENCE: 2
cggccctgca ggttcgcggg aatcagatgt gc                       32
```

```
<210> SEQ ID NO 3
<211> LENGTH: 33
<212> TYPE: DNA
<213> ORGANISM: Artificial Sequence
<220> FEATURE:
<223> OTHER INFORMATION: primer sequence

<400> SEQUENCE: 3
aggagatata ccatgaaaag cttttctgta ctc                          33

<210> SEQ ID NO 4
<211> LENGTH: 44
<212> TYPE: DNA
<213> ORGANISM: Artificial Sequence
<220> FEATURE:
<223> OTHER INFORMATION: primer sequence

<400> SEQUENCE: 4
agcagccgga tcccctgcag gactagttta ctggctggtg ctac              44

<210> SEQ ID NO 5
<211> LENGTH: 39
<212> TYPE: DNA
<213> ORGANISM: Artificial Sequence
<220> FEATURE:
<223> OTHER INFORMATION: primer sequence

<400> SEQUENCE: 5
caccagccag taagctagca aggagatata ccatggctg                    39

<210> SEQ ID NO 6
<211> LENGTH: 37
<212> TYPE: DNA
<213> ORGANISM: Artificial Sequence
<220> FEATURE:
<223> OTHER INFORMATION: primer sequence

<400> SEQUENCE: 6
tcccctgcag gactagttta caggcgagaa cgggtag                      37
```

PROCESS FOR THE PRODUCTION OF METHYL METHACRYLATE

FIELD OF THE INVENTION

The present invention relates to a process for the production of methyl methacrylate. In particular, the invention relates to a process for producing methyl methacrylate via fermentation to produce $C_3$-$C_{12}$ methacrylate ester.

BACKGROUND TO THE INVENTION

Methyl methacrylate (MMA) is an important monomer in the chemical industry. The principal use of MMA is in the production of plastics for various applications; however, MMA can also be used in bone cements for use in orthopaedic surgery. The most significant polymerisation application is the casting, moulding or extrusion of polymethyl methacrylate (PMMA) to produce high optical clarity plastics. The global consumption of PMMA is estimated at approximately 2.1 million tonnes per annum.

MMA is currently produced solely by chemical means and current methods for the production of MMA include the acetone cyanohydrin (ACH) route and other routes starting from various $C_2$-$C_4$ precursors. One of the most successful methods for producing MMA is the 'Alpha process' whereby MMA is obtained from the ester, methyl propionate, by anhydrous reaction with formaldehyde. In the Alpha process, the methyl propionate is produced by the carbonylation of ethylene. This ethylene feedstock is derived from fossil fuels. The Alpha process offers many advantages compared to other processes commonly used in the production of MMA. These advantages include a reduction in the use of hazardous chemicals, much higher product selectivity, and a reduced reliance on crude oil derived feedstocks. However, the pricing of the feedstock is linked to the cost of gasoline. It would therefore be desirable to develop an alternative process for the production of MMA which overcomes these deficiencies.

Microorganisms can be used to produce high value chemicals via fermentation, rather than by chemical synthesis. Recombinant DNA technology and synthetic metabolic engineering of such microorganisms has allowed for the reconstruction of metabolic pathways towards the production of specific chemicals. Several sustainable routes towards the bioproduction of acrylates have recently been undergoing development. These methods have generally focused on the production of acrylates from renewable feedstocks via microbial fermentation. However, accumulation of these products during fermentation is generally toxic to the biocatalysts, inhibiting cell growth and/or resulting in cell death. In particular, higher alkyl methacrylates (such as butyl methacrylate (BMA) for example) exhibit even higher toxicity towards the biocatalysts than lower alkyl methacrylates such as MMA. In view of this, and the given disadvantages associated with current chemical processes for producing MMA, it would be advantageous to provide an improved biological or part-biological process for the production of MMA.

It is an object of the present invention to obviate or mitigate one or more of the abovementioned problems, to provide an improved process for the production of MMA and/or provide an improved biological or part-biological process for the production of MMA.

SUMMARY OF THE INVENTION

The present invention relates to a process for the production of MMA and is based, in part, on studies by the inventors in which they have surprisingly shown that it is possible to effectively produce MMA via a fermentation that produces higher methacrylate esters, despite the inherent toxicity that said higher methacrylates exhibit towards microorganisms. It has also surprisingly been found that the process of the present invention provides improved reaction rate for higher esters compared with the direct production of MMA.

In a first aspect of the present invention there is provided a process for the production of methyl methacrylate (MMA). The process comprises the steps of:
  a) providing a microorganism in a fermentation medium, under conditions which said microorganism will produce a $C_3$-$C_{12}$ methacrylate ester;
  b) providing an organic phase in contact with the fermentation medium, said organic phase including $C_3$-$C_{12}$ methacrylate ester in a higher concentration than that in the fermentation medium;
  c) removing organic phase containing the said $C_3$-$C_{12}$ methacrylate ester from contact with the fermentation medium; and
  d) transesterifying the removed $C_3$-$C_{12}$ methacrylate ester with methanol, optionally after separation from the organic phase, to produce methyl methacrylate.

$C_3$-$C_{12}$ Methacrylate Esters

In the first aspect of the present invention, $C_3$-$C_{12}$ methacrylate esters are produced by microorganisms in a fermentation medium.

By the term $C_3$-$C_{12}$ methacrylate esters is generally meant a methacrylate comprising a $C_3$-$C_{12}$ alkyl, hydroxyalkyl, alkenyl, alkylaryl or alkenylaryl group including structural isomers thereof. The $C_3$-$C_{12}$ group may be cyclic, acyclic, or part cyclic, linear or branched, aliphatic, aromatic or part-aromatic/aliphatic. Preferably the $C_3$-$C_{12}$ methacrylate esters of the present invention may include, for example, n-propyl, isopropyl, isobutyl, n-butyl, t-butyl, isopentyl, hexyl, cyclohexyl, 2-ethylhexyl, decyl, dodecyl, hydroxyethyl, hydroxypropyl, isobornyl, allyl or cinnamyl methacrylate.

Preferably the $C_3$-$C_{12}$ methacrylate esters are $C_3$-$C_{12}$ alkyl methacrylates, more preferably, $C_3$-$C_8$ alkyl methacrylates for example n-propyl, isopropyl, isobutyl, n-butyl, isopentyl, hexyl, cyclohexyl, heptyl, octyl, 2-ethylhexyl, decyl or dodecyl methacrylate.

Preferably, the hydroxyalkyl methacrylates are hydroxyethyl or hydroxypropyl methacrylate.

In embodiments, the $C_3$-$C_{12}$ methacrylate esters are $C_3$-$C_{12}$ alkenylaryl methacrylates, for example cinnamyl methacrylate.

The $C_3$-$C_{12}$ alkyl methacrylates are more preferably $C_3$-$C_6$ alkyl methacrylates, such as the propyl, butyl or hexyl methacrylates, including for example, structural isomers thereof. More preferably, the $C_3$-$C_6$ alkyl methacrylates are propyl or butyl methacrylates, in particular isopropyl or n-butyl methacrylate.

Microorganisms

The microorganisms of the present invention may be selected from naturally-occurring wildtype or non-naturally occurring recombinant microorganism/s, for example, bacteria, archaea, yeast, fungus, algae or any of a variety of other microorganism/s applicable to fermentation processes.

In embodiments of the invention, the microorganism/s are bacteria. Examples of suitable bacteria include enterobacteria belonging to proteobacteria of the genus *Escherichia, Enterobacter, Pantoea, Klebsiella, Serratia, Erwinia, Salmonella, Morganella*, or the like, so-called coryneform bacteria belonging to the genus *Brevibacterium, Corynebac-* terium or *Microbacterium* and bacteria belonging to the genus *Alicyclobacillus, Bacillus, Hydrogenobacter, Methanococcus, Acetobacter, Acinetobacter, Agrobacterium, Axorhizobium, Azotobacter, Anaplasma, Bacteroides, Bartonella, Bordetella, Borrelia, Brucella, Burkholderia, Calymmatobacterium, Campylobacter, Chlamydia, Chlamydophila, Clostridium, Coxiella, Ehrlichia, Enterococcus, Francisella, Fusobacterium, Gardnerella, Haemophilus, Helicobacter, Kelbsiella, Methanobacterium, Micrococcus, Moraxella, Mycobacterium, Mycoplasma, Neisseria, Pasteurella, Peptostreptococcus, Porphyromonas, Prevotella, Pseudomonas, Rhizobium, Rickettsia, Rochalimaea, Rothia, Shigella, Staphylococcus, Stenotrophomonas, Streptococcus, Treponema, Vibrio, Wolbachia, Yersinia,* or the like.

Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtils, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens, Hydrogenobacter thermophilus, Methanococcus jannaschii* and *Pseudomonas putida.*

Preferably the bacterium is of the genus *Escherichia, Corynebacterium* or *Pseudomonas.* Preferably the bacterium is *Escherichia coli, Corynebacterium glutamicum, Pseudomonas fluorescens* or *Pseudomonas putida.*

Exemplary yeasts or fungi include those belonging to the genera *Saccharomyces, Schizosaccharomyces, Candida, Kluyveromyces, Aspergillus, Pichia, Cryptococcus,* or the like. Exemplary yeast or fungi species include those selected from *Saccharomyces cerevisiae, Schizosaccharomyces pombe, Kluyveromyces lactis, Kluyveromyces marxianus, Aspergillus terreus, Aspergillus niger, Pichia pastoris,* or the like.

In embodiments of the present invention, the microorganisms may be genetically modified to produce more $C_3$-$C_{12}$ methacrylate ester than the wildtype.

Enhancing the production of $C_3$-$C_{12}$ methacrylate ester compared to a wildtype microorganism may include making modifications to existing cellular metabolic processes, nucleic acids and/or proteins by the use of various genetic engineering techniques known in the art. Enhancing the production of $C_3$-$C_{12}$ methacrylate ester may also include modifying the microorganism/s to express one or more heterologous genes in the microorganism/s. These may include genes encoding enzymes of the desired pathway to $C_3$-$C_{12}$ methacrylate ester from carbon based feedstocks, or may include other auxiliary genes which act to promote the functioning and expression of the enzymes in such pathways either directly or indirectly.

Accordingly, microorganism/s of the present invention may be modified to enhance production of $C_3$-$C_{12}$ methacrylate esters.

The microorganisms may comprise modifications which decrease or eliminate the activity of an enzyme that catalyses synthesis of a compound other than $C_3$-$C_{12}$ methacrylate esters by competing for the same substrates and/or intermediates. Alternatively, or in addition, the microorganisms used in the process of the present invention may comprise modifications that decrease or eliminate the activity of an enzyme which metabolises $C_3$-$C_{12}$ methacrylate esters or metabolises an intermediate in a pathway producing $C_3$-$C_{12}$ methacrylate esters.

Alternatively, or in addition, the microorganisms used in the process of the present invention may comprise modifications which decrease or eliminate the activity of proteins involved in other cellular functions that remove intermediates. Examples of such other cellular functions may include storage mechanisms such as vacuolar storage (e.g. in yeasts) or other intracellular bodies capable of storing metabolites (e.g. bacterial microcompartments), the bacterial periplasm or transport mechanisms such as transmembrane pumps or porins capable of exporting metabolites.

Alternatively, or in addition, the microorganisms used in the process of the present invention may comprise modifications to reduce or eliminate the activity of an enzyme or protein partaking in a cellular function which:

(i) diverts material from $C_3$-$C_{12}$ methacrylate ester producing pathways; and/or (ii) metabolises $C_3$-$C_{12}$ methacrylate ester.

Alternatively, or in the addition, the microorganisms used in the process of the present invention may comprise modifications which result in the microorganism being more resistant to the fermentation conditions, reaction conditions or other stresses encountered during the process of the present invention.

Enhancing the production of $C_3$-$C_{12}$ methacrylate ester may include selecting microorganisms which are adapted to produce more $C_3$-$C_{12}$ methacrylate ester compared to a wildtype microorganism. In the context of the present invention, the term 'adapted', when used with respect of a microorganism, means a genetically modified or engineered organism, or a mutant strain of an organism which, for example, has been selected on the basis that it expresses one or more enzymes which result in enhanced production of $C_3$-$C_{12}$ methacrylate ester naturally. Such modifications may include any of the abovementioned modifications which may enhance production of $C_3$-$C_{12}$ methacrylate esters.

In order to reduce or eliminate the activities of the aforementioned enzymes or proteins, mutations for reducing or eliminating intracellular activities of the enzymes or proteins can be introduced into the genes of the aforementioned enzymes or proteins by conventional random or site directed mutagenesis or genetic engineering techniques. Examples of the mutagenesis can include, for example, X-ray or ultraviolet ray irradiation, treatment with a mutagen such as N-methyl-N'-nitro-N-nitrosoguanidine, in vitro site directed or random mutagenesis by high fidelity or error-prone polymerase chain reaction, respectively, and so forth. The site on the gene where the mutation is introduced can be in the coding region encoding the enzyme or protein or an expression control region such as a promoter. Examples of genetic engineering techniques can include genetic recombination, transduction, cell fusion and gene knockouts.

A decrease or elimination of the intracellular activity of the objective enzyme or protein and the degree of decrease can be confirmed by measuring the enzyme or protein activity in a cell extract or a purified fraction thereof obtained from a candidate strain, and comparing it with that of a wildtype strain, or by measuring formation of the target product by whole cells.

Preferably the one or more microorganism/s express one or more enzymes necessary to catalyse the production of $C_3$-$C_{12}$ methacrylate esters, preferably $C_3$-$C_{12}$ alkyl methacrylates. Preferably, the relevant step/s and any further enzymatic steps are conducted in vivo, within the one or more microorganism/s.

The one or more microorganism/s may express the one or more enzymes naturally, or may be genetically engineered to express the one or more enzymes, or may express a combination of both wildtype or genetically engineered enzymes. Such a genetically engineered organism may be described as a recombinant organism.

The one or more microorganism/s may express the one or more enzymes endogenously or heterologously, or a combination of endogenous and heterologous enzymes.

In the context of the present invention, the term 'recombinant organism' means a genetically modified or engineered organism comprising genetic material which has been artificially constructed and inserted into the organism. The genetic material may comprise endogenous or heterologous nucleic acids which may or may not have been further genetically modified.

In the context of the present invention, the term 'endogenous' means deriving from the same species of organism.

In the context of the present invention, the term 'heterologous' means deriving from a different species of organism.

The one or more gene/s which may be expressed within the microorganism/s such that it is modified to produce $C_3$-$C_{12}$ methacrylate ester, preferably $C_3$-$C_{12}$ alkyl methacrylate include those encoding any of the following enzymes.

In embodiments, the microorganism may express one or more enzymes which can convert isobutyryl-CoA to methacrylyl-CoA, for example an oxidase, dehydrogenase or oxidoreductase.

The oxidase may be an oxidase acting on CH—CH bonds, under EC number 1.3.x.x, more preferably an oxidase acting on CH—CH bonds using oxygen as an electron acceptor, under EC number EC 1.3.3.x. Still more preferably, the oxidase is an acyl-CoA oxidase, suitably under EC number EC 1.3.3.6. More preferably the acyl-CoA oxidase is selected from any of the following enzymes: ACX4 from *Arabidopsis thaliana*, short chain acyl-CoA oxidase from *Arthrobacter nicotianae*, peroxisomal acyl-CoA oxidase from *Vigna radiata*, acyl-CoA oxidase from *Candida* sp. and acyl-CoA oxidase 4 from *Candida tropicalis*. Most preferably the acyl-CoA oxidase is ACX4 from *Arabidopsis thaliana*.

The oxidoreductase, may be an oxidoreductase under EC group number 1.X.X.X. Preferably, the oxidoreductase is an oxidoreductase acting on the CH—CH group of electron donors, suitably under EC group 1.3.X.X. More preferably, the oxidoreductase acting on the CH—CH group of donors is a FAD dependent oxidoreductase, still more preferably the oxidoreductase is a CoA dehydrogenase under EC group 1.3.8.X. More preferably still, the oxidoreductase is a short chain acyl-CoA dehydrogenase, suitably under EC group 1.3.8.1, an isovaleryl-CoA dehydrogenase, suitably under EC group 1.3.8.4, a 2-methyl-branched-chain acyl-CoA dehydrogenase, suitably under EC group 1.3.8.5 or an acyl-CoA dehydrogenase, suitably under EC group 1.3.8.-, such as an isobutyryl-CoA dehydrogenase. Most preferably the oxidoreductase is selected from any of the following enzymes: short/branched chain acyl-CoA dehydrogenase from *Pseudomonas putida*, isobutyryl-CoA dehydrogenase from *Homo sapiens* and isovaleryl-CoA dehydrogenase from *Arabidopsis thaliana*.

The CoA dehydrogenase enzymes generally require an associated electron transport system to couple oxidation of the substrate with reduction of ubiquinone, which is then regenerated. Such an electron transport system consists of an electron transfer flavoprotein (ETF), and an electron transfer flavoprotein ubiquinone oxidoreductase (ETFQO). The ETF must be compatible with both the acyl-CoA dehydrogenase enzyme and the ETFQO. Accordingly, in the embodiments where an acyl-CoA dehydrogenase is used, one of the following regeneration systems is preferably employed:

a host microorganism expressing an endogenous CoA dehydrogenase, with activity on isobutyryl-CoA, and its associated electron transport system, such as is in the case of, for example, *Pseudomonas putida*;

a host microorganism expressing a heterologous CoA dehydrogenase enzyme accompanied by the proteins of the electron transport system from the same organism as the heterologous CoA dehydrogenase. For example, the CoA dehydrogenase and electron transport system components from *Homo sapiens, Pseudomonas putida, Paracoccus denitrificans*, or from *Arabidopsis thaliana*, all expressed in *Escherichia coli* (or another host organism); or a host microorganism expressing a heterologous CoA dehydrogenase enzyme, accompanied by electron transport system components also from different microorganisms, whereby those components are compatible with each other and with the CoA dehydrogenase. For example, the CoA dehydrogenase from *Homo sapiens* is compatible with the electron transfer flavoprotein of *Sus scrofa* which is in turn compatible with the electron transfer flavoprotein ubiquinone oxidoreductase from *Rhodobacter sphaeroides*. Alternatively, as the ETF-ubiquinone oxidoreductase of *A. thaliana* has good sequence homology with the ETF-ubiquinone oxidoreductase of *R. sphaeroides,* isovaleryl-CoA dehydrogenase and the ETF of *A. thaliana* could form a functional system with the ETF-ubiquinone oxidoreductase from *R. sphaeroides* for the oxidation of isobutyryl-CoA. Finally, the ETF and ETF-ubiquinone oxidoreductase from *Paracoccus denitrificans* are predicted to be compatible with an isobutyryl-CoA dehydrogenase from another source, such as that of *H. sapiens* or homologues from different organisms, due to the similarity of the *P. denitrificans* ETF with the human and porcine ETFs.

In embodiments, the microorganism may express one or more enzymes which can convert methacrylyl-CoA to a $C_3$-$C_{12}$ methacrylate ester, for example an alcohol acyltransferase.

Preferably, the alcohol acyltransferase acts in the presence of an alcohol, more preferably C3-C12 alcohol, most preferably, a C3-C8 alcohol, still more preferably in the presence of propanol or butanol, such as, n-propanol, isopropanol, n-butanol, isobutanol, sec-butanol, tert-butanol, pentanols, hexanols, heptanols or octanols. Most preferably, the alcohol acyltransferase acts in the presence of isopropanol or n-butanol.

By the term alcohol herein is meant a species having a hydroxyl group (—OH group) and which is capable of forming an ester group with the methacrylate.

Preferably the alcohol acyltransferase is derived from a plant origin, more preferably the plant belongs to any order selected from the group consisting of Zingiberales, Rosales, Ericales, Cucurbitales, Brassicales and Laurales; still more preferably the plant belongs to any family selected from the group consisting of Musaceae, Rosaceae, Ericaceae, Actinidiaceae, Cucurbitaceae, Caricaceae and Lauraceae; still more preferably the plant belongs to any genus selected from the group consisting of *Musa, Fragaria, Malus, Prunus, Pyrus, Vaccinium, Actinidia, Cucumis, Carica* and *Persea*; still more preferably the plant is any one selected from the group consisting of banana, strawberry, apple, *Prunus mume, Pyrus communis*, blueberry, kiwi, melon, papaya and avocado. Most preferably, the alcohol acyltransferase is derived from a fruit origin such as apple, melon or tomato origin, suitably apple origin.

In embodiments of the present invention the microorganism may express an oxidase and an alcohol acyltransferase for converting isobutyryl CoA to a $C_3$-$C_{12}$ methacrylate ester. Suitable oxidases and alcohol acyltransferases are outlined above. It is particularly preferred if the oxidase is ACX4 from *Arabidopsis thaliana*.

In embodiments, the microorganism may express one or more enzymes which can convert 2-ketoisovaleric acid to isobutyryl-CoA. In embodiments, the one or more enzymes may be an enzyme complex such as a branched chain keto acid dehydrogenase enzyme complex, consisting of the alpha subunit component, the lipoamide acyltransferase component and the lipoamide dehydrogenase component. Most preferably, the dehydrogenase is selected from any of the following enzymes: branched chain keto acid dehydrogenase (BCKD) from *P. putida*, BCKD from *Bacillus subtilis*, BCKD from *P. aeuruginosa*, BCKD from *A. thaliana*, BCKD from *Streptomyces coelicolor* and BCKD from *Thermus thermophilus*.

Alternatively, the conversion of 2-ketoisovaleric acid to isobutyryl-CoA may be catalysed by an oxidoreductase enzyme, suitably under EC group 1.X.X.X, preferably an oxidoreductase acting on the aldehyde or oxo group of donors, suitably under EC group 1.2.X.X, more preferably an oxidoreductase enzyme acting on the aldehyde or oxo group of donors, using an iron-sulfur protein as the electron acceptor, suitably under EC group 1.2.7.X, most preferably a 2-ketoisovalerate ferredoxin reductase (known also as ketovaline ferredoxin oxidoreductases), suitably under EC group number 1.2.7.7, which is a tetramer consisting alpha, beta, gamma and delta subunits. Examples of such enzymes are 2-ketoisovalerate ferredoxin reductase from *Pyrococcus furiosis*; 2-ketoisovalerate ferredoxin reductase from *Pyrococcus sp.*; 2-ketoisovalerate ferredoxin reductase from *Thermococcus sp*; 2-ketoisovalerate ferredoxin reductase from *Thermococcus litoralis*; 2-ketoisovalerate ferredoxin reductase from *Thermococcus profundus* and 2-ketoisovalerate ferredoxin reductase from *Methanobacterium thermoautotrophicum*.

Alternatively, the microorganism may express one or more enzymes which can convert isobutyric acid to isobutyryl-CoA, for example a ligase. The ligase is suitably under EC group number 6.X.X.X, preferably a carbon-sulfur bond forming ligase under EC group 6.2.X.X, more preferably an acid-thiol forming ligase under EC group 6.2.1.X, more preferably a GDP-forming, an ADP forming or an AMP forming ligase, such as an AMP forming acetate-CoA ligase, suitably under EC group 6.2.1.1, a butyrate-CoA ligase, suitably under EC group 6.2.1.2, a carboxylic acid-CoA ligase, suitably under EC group 6.2.1.10, an ADP forming acetate-CoA ligase, suitably under EC group 6.2.1.13, a propionate-CoA ligase, suitably under EC group 6.2.1.17 or an acid-thiol ligase in EC group 6.2.1.-. Most preferably the ligase is selected from any of the following enzymes: AcsA from *Pseudomonas chlororaphis*, butyryl-CoA synthetase from *Paecilomyces varioti*, butyryl-CoA synthetase from bovine heart mitochondria.

Alternatively, the microorganism may express one or more enzymes which can convert isobutyrate to isobutyryl-CoA. For example, isobutyrate may be converted to isobutyryl-phosphate by a kinase enzyme and isobutyryl-phosphate may be converted to isobutyryl-CoA by a transferase enzyme.

Preferably the isobutyrate is converted to isobutyryl-phosphate by a kinase enzyme, suitably under EC group number EC 2.X.X.X, preferably under EC 2.7.X.X, more preferably under EC group number EC 2.7.2.X, most preferably an acetate kinase, suitably under EC group 2.7.2.1, a formate kinase under EC 2.7.2.6, a butyrate kinase under EC 2.7.2.7, a branched chain fatty acid kinase under EC 2.7.2.14 or a propionate kinase under EC 2.7.2.15. Most preferably the kinase is selected from any of the following enzymes: branched chain fatty acid kinase from Spirochete MA-2, butyrate kinase from *C. butyricum*.

Preferably the isobutyryl-phosphate is converted to isobutyryl-CoA by the action of a transferase enzyme, under EC group number 2.X.X.X, more preferably by the action of an acyltransferase under EC group number 2.3.X.X, still more preferably by the action of acyltransferase transferring groups other than amino-acyl groups under EC group number 2.3.1.X. Still more preferably a phosphate acetyltransferase or a phosphate butyryltransferase, under EC group numbers 2.3.1.8 and 2.3.1.19, respectively. More preferably the transferase is phosphate butyryltransferase from *Clostridium acetobutylicum* ATCC824 or phosphate acetyltransferase from *Bacillus subtilis, Corynebacterium glutamicum* ATCC13032, *Thermotoga maritima* and *Clostridium kluyveri*. Other sources of these enzymes include other anaerobic bacteria, especially *Clostridium* species such as *Clostridium pasteurianum* or *Clostridium beijerinckii*.

The microorganism may express one or more enzymes which can convert isobutyric acid to isobutyryl-CoA, for example a synthetase enzyme, preferably an isobutyryl-CoA synthetase, most preferably isobutyryl-CoA synthetase (AcsA) from P. chloraphis B23.

Optionally, the microorganism may express any combination of the above described enzymes.

Sources of nucleic acids for genes encoding the proteins, in particular the enzymes expressed in the microorganism/s according to the present invention can include, for example, any species where the encoded gene product is capable of catalysing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Homo sapiens, Propionibacterium fredenreichii, Methylobacterium extorquens, Shigella flexneri, Salmonella enterica, Yersinia frederiksenii, Propionibacterium acnes, Rattus norvegicus, Caenorhabditis elegans, Bacillus cereus, Acinetobacter calcoaceticus, Acinetobacter baylyi, Acinetobacter sp., Clostridium kluyveri, Pseudomonas sp., Thermus thermophilus, Pseudomonas aeruginosa, Pseudomonas putida, Oryctolagus cuniculus, Clostridium acetobutylicum, Leuconostoc mesenteroides, Eubacterium barkeri, Bacteroides capillosus, Anaerotruncus colihominis, Natranaerobius thermophilus, Campylobacter jejuni, Arabidopsis thaliana, Corynebacterium glutamicum, Sus scrofa, Bacillus subtilus, Pseudomonas fluorescens, Serratia marcescens, Streptomyces coelicolor, Methylibium petroleiphilum, Streptomyces cinnamonensis, Streptomyces avermitilis, Archaeoglobus fulgidus, Haloarcula marismortui, Pyrobaculum aerophilum, Saccharomyces cerevisiae, Clostridium cochlearium, Clostridium tetanomorphum, Clostridium tetani, Citrobacter amalonaticus, Ralstonia eutropha, Mus musculus, Bos taurus, Fusobacterium nucleatum, Morganella morganii, Clostridium pasteurianum, Rhodobacter sphaeroides, Xanthobacter autotrophicus, Clostridium propionicum, Megasphaera elsdenii, Aspergillus terreus, Candida, Sulfolobus tokodaii, Metallosphaera sedula, Chloroflexus aurantiacus, Clostridium saccharoperbutylacetonicum,*

*Acidaminococcus fermentans, Helicobacter pylori*, as well as other exemplary species disclosed herein or available as source organisms for corresponding genes.

Methods for constructing and testing the expression of a protein in a non-naturally occurring $C_3$-$C_{12}$ methacrylate ester producing microorganism can be performed, for example, by recombinant techniques and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

Exogenous nucleic acid sequences involved in a pathway for production of $C_3$-$C_{12}$ methacrylate ester or an intermediate in the formation thereof can be introduced stably or transiently into a microorganism cell using techniques well known in the art including, but not limited to, conjugation, electroporation, chemical transformation, transduction, transfection, and ultrasound transformation.

Examples of transformation methods can include treating recipient microorganism/s cells with calcium chloride so to increase permeability of the DNA, and preparing competent cells from cells which are in the growth phase, followed by transformation with DNA. Alternatively, a method of making DNA-recipient cells into protoplasts or spheroplasts, which can easily take up recombinant DNA, followed by introducing the recombinant DNA into the cells, which is known to be applicable to *Bacillus subtilis*, actinomycetes and yeasts can also be employed. In addition, transformation of microorganisms can also be performed by electroporation. Such methods are well known in the art.

For exogenous expression in *E. coli* or other prokaryotic microorganism cells, some nucleic acid sequences in the genes or cDNAs of eukaryotic nucleic acids can encode targeting signals such as an N-terminal mitochondrial or other targeting signal, which can be removed before transformation into prokaryotic microorganism cells, if desired. For example, removal of a mitochondrial leader sequence led to increased expression in *E. coli* (Hoffmeister et al., J. Biol. Chem. 280:4329-4338 (2005). For exogenous expression in yeast or other eukaryotic microorganism cells, genes can be expressed in the cytosol without the addition of leader sequence, or can be targeted to mitochondria or other organelles, or targeted for secretion, by the addition of a suitable targeting sequence such as a mitochondrial targeting or secretion signal suitable for the target organelle. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins within the microorganism/s.

An expression vector or vectors can be constructed to include one or more biosynthetic pathway enzyme(s) encoding nucleic acids as exemplified herein operably linked to expression control sequences functional in the microorganism/s. Expression vectors applicable for use in the microorganism/s of the invention include, for example, plasmids, cosmids, phage vectors, viral vectors, episomes and artificial chromosomes, including vectors and selection sequences or markers operable for stable integration into a host chromosome.

Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive, inducible or repressible promoters, transcription enhancers, transcription terminators, translation signals and the like which are well known in the art. When two or more exogenous encoding nucleic acid sequences are to be co-expressed, both nucleic acid sequences can be inserted, for example, into a single expression vector or in separate expression vectors. For single vector expression, the encoding nucleic acids can be operationally linked to one common expression control sequence or linked to different expression control sequences, such as inducible promoters and constitutive promoters. In some embodiments, the vector may have two or more promoters for the co-expression of multiple genes or operons. In some embodiments, the genes/operons may be expressed on one or more different vectors with one or more corresponding promoters.

The vector used for transformation can be a vector autonomously replicable in a cell of the microorganism/s. Examples of vectors autonomously replicable in bacteria of the Enterobacteriaceae bacteria such as *E. coli* can include plasmid vectors pUC19, pUC18, pBR322, RSF1010, pHSG299, pHSG298, pHSG399, pHSG398, pSTV28, pSTV29, pET20b(+), pET28b(+) (pET vectors are available from Novagen), pLysS, (pHSG and pSTV vectors are available from Takara Bio Inc.), pMW119, pMW118, pMW219, pMW218 (pMW vectors are available from Nippon Gene Co., Ltd.) and so forth, and their derivatives. Furthermore, vectors for coryneform bacteria can include pAM330 (Japanese Patent Laid-open No. 58-67699), pHM1519 (Japanese Patent Laid-open No. 58-77895), pSFK6 (Japanese Patent Laid-open No. 2000-262288), pVK7 (USP2003-0175912A), pAJ655, pAJ611, pAJ1844 (Japanese Patent Laid-open No. 58-192900), pCG1 (Japanese Patent Laid-open No. 57-134500), pCG2 (Japanese Patent Laid-open No. 58-35197), pCG4, pCG11 (Japanese Patent Laid-open No. 57-183799), pHK4 (Japanese Patent Laid-open No. 5-7491) and so forth. Furthermore, vectors for yeast can include yeast plasmids, such as for example pD902 or pD905 for *Pichia pastoris*, or pD1201, pD1204, pD1205, pD1207, pD1211, pD1214 pD1215, pD1217, pD1218, pD1221, pD1224, pD1225, pD1227, pD1231, pD1234, pD1235, pD1237 for *Saccharomyces cerevisiae*. Genes can also be integrated into the host chromosome, using well known methods (e.g. Datensko and Wanner (Datsenko, K. A. and Wanner, B. L. 2000, Proc. Natl. Acad. Sci. USA, 97:6640-6645)).

Enhancement of the activity of an enzyme can include enhancing expression of a target gene by replacing an expression regulatory sequence of the target gene such as a promoter on the genomic DNA or plasmid with a promoter which has an appropriate strength. For example, the thr promoter, lac promoter, trp promoter, trc promoter, pL promoter, tac promoter, etc., are known as frequently used promoters. Examples of promoters with high expression activity in microorganisms such as bacteria can include promoters of the elongation factor Tu (EF-Tu) gene, tuf, promoters of genes that encode co-chaperonin GroES/EL, thioredoxin reductase, phosphoglycerate mutase, glyceraldehyde-3-phosphate dehydrogenase, and the like (WO2006/028063, EP1697525). Examples of strong promoters and methods for evaluating the strength of promoters are well known in the art.

Moreover, it is also possible to substitute several nucleotides in a promoter region of a gene, so that the promoter has an appropriate strength, as disclosed in WO 2000/18935. Substitution of the expression regulatory sequence can be performed, for example, in the same manner as in gene substitution using a temperature sensitive plasmid. Examples of vectors having a temperature sensitive replication origin which can be used for *Escherichia coli* or *Pantoea ananatis* can include, for example, plasmid pMAN997 described in International Publication WO 1999/03988, its derivative, and so forth. Furthermore, substitution of an expression regulatory sequence can also be performed by methods which employ linear DNA, such as a method called "Red-driven integration" using Red recombinase of λ-phage (Datsenko, K. A. and Wanner, B. L. 2000, Proc. Natl. Acad. Sci. USA, 97:6640-6645), a method combining the Red-driven integration method and the λ-phage excisive system (Cho, E. H. et al. 2002. J. Bacteriol. 184:5200-5203) (WO2005/010175), and so forth. The modification of an expression regulatory sequence can be combined with increasing the gene copy number.

Furthermore, it is known that substitution of several nucleotides in a spacer between the ribosome binding site (RBS) and the start codon, and particularly, the sequences immediately upstream of the start codon profoundly affect the mRNA translatability. Translation can be enhanced by modifying these sequences.

When a target gene is introduced into the aforementioned plasmid or chromosome, any promoter can be used for expression of the gene so long as a promoter that functions in the microorganism/s used is chosen. The promoter can be the native promoter of the gene, or a modified promoter. Expression of a gene can also be controlled by suitably choosing a promoter that potently functions in the chosen microorganism/s, or by approximating −35 and −10 regions of a promoter close to the consensus sequence.

The transformation, transduction, conjugational or chromosomal insertion of exogenous nucleic acid sequences involved in a metabolic or synthetic pathway can be confirmed using methods well known in the art. Such methods include, for example, extraction of plasmid or chromosomal DNA followed by polymerase chain amplification of specific target sequences, or restriction mapping, further nucleic acid analysis such as Northern blots or polymerase chain reaction (PCR) amplification of mRNA, or polyacrylamide gel electrophoresis, or enzymatic activity measurements, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired gene product, and it is further understood that expression levels can be optimized to obtain sufficient expression using methods well known in the art.

It should be noted that the one or more genes encoding enzymes which may be expressed in microorganism/s of the invention also comprise genes encoding variants of said enzymes, for example, variant enzymes which include substitutions, deletions, insertions or additions of one or several amino acids in the polypeptide sequence, and wherein said polypeptide retains the activity of the unmodified enzyme. Such variant enzymes also include variant enzymes which have a reduced enzymatic activity when compared to the unmodified enzyme and enzymes with modified allosteric control.

Further methods for imparting or enhancing $C_3$-$C_{12}$ methacrylate ester producing ability and/or intermediates thereof can include imparting resistance to down-regulators/inhibitors, imparting sensitivity to up-regulators/activators or alleviating the need for allosteric activation of enzymes by other compounds.

Solvent Extraction

In the process of the present invention, an organic phase is provided in contact with the fermentation medium, the organic phase including $C_3$-$C_{12}$ methacrylate ester, preferably $C_3$-$C_{12}$ alkyl methacrylate in a higher concentration than that in the fermentation medium.

The production of $C_3$-$C_{12}$ methacrylate ester, such as butyl methacrylate, offers the advantage of phase separation from fermentation medium at high concentrations as the solubility limit is reached. Therefore if the titre of $C_3$-$C_{12}$ methacrylate ester in the fermentation medium is sufficiently high, the need for an additional extraction solvent may be negated and the ester will then form its own organic phase.

Preferably the titre of $C_3$-$C_{12}$ methacrylate ester in the fermentation medium is at least 5 mg/l. For example, 5, 15, 25, 35, 45, 55, 65, 75, 85, 95, 105, 115, 125, 135, 145, 155 mg/l. More preferably the titre is greater than 160 mg/l, 180 mg/l, 200 mg/l, 220 mg/l or 240 mg/l.

In preferred embodiments the titre of $C_3$-$C_{12}$ methacrylate ester in the fermentation medium is at the solubility limit for the fermentation medium so that the $C_3$-$C_{12}$ methacrylate ester separates out to form an organic phase in contact therewith.

In embodiments where the $C_3$-$C_{12}$ methacrylate ester is butyl methacrylate, it is particularly preferred that the titre of butyl methacrylate in the fermentation medium is at least 120, 130, 140, 150 or 200 mg/l. Even more preferred is a titre of butyl methacrylate at the solubility limit in the fermentation medium, approximately 220 mg/l. At such a concentration, the need for an additional extraction solvent may be negated.

Therefore, in embodiments of the present invention, the organic phase provided in step b) may be provided by the $C_3$-$C_{12}$ methacrylate ester produced by the microorganism. Alternatively, in embodiments the organic phase provided in step b) may comprise an external organic solvent in contact with (for example added to) the fermentation medium, either prior to, during or after fermentation. For example, the organic solvent may be added to the fermentation medium as a layer (for example a layer on top of the fermentation medium) either prior to, during or after fermentation. The external organic solvent is preferably effective to extract $C_3$-$C_{12}$ methacrylate ester from the fermentation medium during contact therewith to typically thereby include said $C_3$-$C_{12}$ methacrylate ester.

In embodiments in which an external organic solvent is contacted with the fermentation medium, the organic phase preferably comprises less than 50% of the total volume of the medium (i.e. the total volume of the fermentation medium and the organic phase). More preferably, in this scenario the organic phase comprises less than 40%, 30% or 20% of the total volume of the medium.

In embodiments in which the organic phase provided in step b) is provided substantially by the $C_3$-$C_{12}$ methacrylate ester produced by the microorganism, the organic phase comprises less than 20% of the total volume of the medium (i.e. the total volume of the fermentation medium and the organic phase). More preferably, in this scenario the organic phase comprises less than 10% or 5% of the total volume of the medium.

In embodiments, the organic solvent is biocompatible, i.e. is not highly toxic to microorganisms.

In embodiments, the organic solvent has a $logP_{o/w}$ value of greater than or equal to 3.0. More preferably, the organic solvent has a logP$_{o/w}$ value of greater than or equal to 3.6, 3.7, 3.8, 3.9 or 4.0. logP$_{o/w}$ is defined as the logarithm of the partition coefficient of a particular solvent between a standardized 1:1 mixture of 1-octanol and water. The present inventors have shown that, with increasing logP$_{o/w}$ value there is a decrease in the resultant microorganism toxicity. Particularly preferred solvents are higher alkanes of C6 and above which may be linear or branched, cyclic alkanes of C7 and above and aromatic compounds, particularly benzene, substituted with one or more substituents of C3 and above, particularly alkyl substituents which may be linear or branched.

In embodiments, the organic solvent is selected from the group consisting of tributyrin, isopropylbenzene, n-propylbenzene, cycloheptane, hexane, heptane, cyclooctane, isooctane, 1,4-diisopropylbenzene, octane, nonane, decane, undecane or dodecane and mixtures thereof.

The organic solvent may also be an ionic liquid. In such embodiments, the organic solvent is selected from the group consisting of trihexyl(tetradecyl)phosphonium bis(2-ethylhexyl)phosphate, trihexyl(tetradecyl)phosphonium dicyanamide, trihexyl(tetradecyl)phosphonium bis(trifluoromethane)sulfonimide, trihexyl(tetradecyl)phosphonium acesulfame, trihexyl(tetradecyl)phosphonium saccharinate, trihexyl(tetradecyl)phosphonium salicylate, trihexyl(tetradecyl)phosphonium trifluoromethanesulfonate, trihexyl(tetradecyl)phosphonium bis(2,4,4-trimethylpentyl)phosphinate, trihexyl(tetradecyl)phosphonium dicyanamide, trihexyl(tetradecyl)phosphonium octanoate, trihexyl(tetradecyl)phosphonium cyclamate, tributyl(octyl)phosphonium bis(trifluoromethane)sulfonimide, tributyl(octyl)phosphonium salicylate, tributyl(octyl)phosphonium trifluoromethanesulfonate, tributyl(octyl)phosphonium acesulfame, tributyl(octyl)phosphonium saccharinate, tributyl(octyl)phosphonium bis(trifluoromethane)sulfonimide, tributyl(methyl)ammonium bis(trifluoromethane)sulfonimide, or tetraoctylammonium acesulfame, or mixtures thereof.

In the present invention, the process includes removing organic phase from contact with the fermentation medium. As will be appreciated by the skilled person, the phrase "removing organic phase" does not necessarily imply that the entire organic phase is removed. Although the entire organic phase (or the majority of the organic phase) may be removed in step c), it will be appreciated that only a portion of the organic phase may be removed at any one time. In a continuous process, the organic phase may be continually removed in balance with ester production in the fermentation medium.

In embodiments, the removal of organic phase in step c) of the process of the present invention may be continuous, i.e. may take place throughout the process. Alternatively, the removal of the organic phase may be discontinuous i.e. may take place at defined points during the process.

In embodiments of the present invention, the process may further comprise purifying the C$_3$-C$_{12}$ methacrylate ester in the organic phase (for example the removed organic phase), for example by distillation.

Transesterification The present invention includes transesterifying the C$_3$-C$_{12}$ methacrylate ester to produce methyl methacrylate.

The transesterification reaction of step d) of the present invention takes place in the presence of methanol and a catalyst.

In embodiments, the transesterification will take place in the presence of a catalyst. Any suitable catalyst may be utilised, for example an acid or base catalyst or a biocatalyst, for example an enzyme such as a lipase.

The catalyst may be a homogeneous or heterogeneous catalyst. In one embodiment, the catalyst may be dissolved in a liquid reaction phase. However, the catalyst may be suspended on a solid support over which the reaction phase may pass. In this scenario, the reaction phase is preferably maintained in a liquid, more preferably, an aqueous phase. Preferably the catalyst is homogeneous.

As will be appreciated by the skilled person, a homogeneous catalyst is a catalyst in the same phase as the reactants, whereas a heterogeneous catalyst is a catalyst in a different phase to that of the reactants.

Preferably the catalyst is a basic salt catalyst. Preferably, the basic catalyst comprises a metal oxide, hydroxide, carbonate, acetate (ethanoate), alkoxide, hydrogencarbonate or salt of a decomposable di- or tri-carboxylic acid, or a quaternary ammonium compound of one of the above; more preferably a Group I or Group II metal oxide, hydroxide, carbonate, acetate, alkoxide, hydrogencarbonate or salt of a di- or tri-carboxylic acid or methacrylic acid. The basic catalyst may also comprise one or more amines. Most preferably, the catalyst is a Group I or Group II metal hydroxide or alkoxide.

Preferably, the catalyst is selected from one or more of the following: LiOH, NaOH, KOH, Mg(OH)$_2$, Ca(OH)$_2$, Ba(OH)$_2$, CsOH, Sr(OH)$_2$, RbOH, NH$_4$OH, Li$_2$CO$_3$, Na$_2$CO$_3$, K$_2$CO$_3$, Rb$_2$CO$_3$, Cs$_2$CO$_3$, MgCO$_3$, CaCO$_3$, SrCO$_3$, BaCO$_3$, (NH$_4$)$_2$CO$_3$, LiHCO$_3$, NaHCO$_3$, KHCO$_3$, RbHCO$_3$, CsHCO$_3$, Mg(HCO$_3$)$_2$, Ca(HCO$_3$)$_2$, Sr(HCO$_3$)$_2$, Ba(HCO$_3$)$_2$, NH$_4$HCO$_3$, Li$_2$O, Na$_2$O, K$_2$O, Rb$_2$O, Cs$_2$O, MgO, CaO, SrO, BaO, Li(OR$^1$), Na(OR$^1$), K(OR$^1$), Rb(OR$^1$), Cs(OR$^1$), Mg(OR$^1$)$_2$, Ca(OR$^1$)$_2$, Sr(OR$^1$)$_2$, Ba(OR$^1$)$_2$, NH$_4$(OR) where R$^1$ is any C1 to C6 branched, unbranched or cyclic alkyl group, being optionally substituted with one or more functional groups; NH$_4$(R$^2$CO$_2$), Li(R$^2$CO$_2$), Na(R$^2$CO$_2$), K(R$^2$CO$_2$), Rb(R$^2$CO$_2$), Cs(R$^2$CO$_2$), Mg(R$^2$CO$_2$)$_2$, Ca(R$^2$CO$_2$)$_2$, Sr(R$^2$CO$_2$)$_2$ or Ba(R$^2$CO$_2$)$_2$, where R$^2$CO$_2$ is acetate; (NH$_4$)$_2$(CO$_2$R$^3$CO$_2$), Li$_2$(CO$_2$R$^3$CO$_2$), Na$_2$(CO$_2$R$^3$CO$_2$), K$_2$(CO$_2$R$^3$CO$_2$), Rb$_2$(CO$_2$R$^3$CO$_2$), Cs$_2$(CO$_2$R$^3$CO$_2$), Mg(CO$_2$R$^3$CO$_2$), Ca(CO$_2$R$^3$CO$_2$), Sr(CO$_2$R$^3$CO$_2$), Ba(CO$_2$R$^3$CO$_2$), (NH$_4$)$_2$(CO$_2$R$^3$CO$_2$), where CO$_2$R$^3$CO$_2$ is oxalate; methylamine, ethylamine, propylamine, butylamine, pentylamine, hexylamine, cyclohexylamine, aniline; R$_4$NOH where R is methyl, ethyl propyl, butyl; diazabicycloundecene and diazabicyclononane.

More preferably, the catalyst is selected from one or more of the following:—LiOH, NaOH, KOH, Mg(OH)$_2$, Ca(OH)$_2$, Ba(OH)$_2$, CsOH, Sr(OH)$_2$, RbOH, NH$_4$OH, Li(OR$^1$), Na(OR$^1$), K(OR$^1$), Rb(OR$^1$), Cs(OR$^1$), Mg(OR$^1$)$_2$, Ca(OR$^1$)$_2$, Sr(OR$^1$)$_2$, Ba(OR$^1$)$_2$, NH$_4$(OR$^1$) where R$^1$ is any C1 to C6 branched, unbranched or cyclic alkyl group, being optionally substituted with one or more functional groups; diazabicycloundecene and diazabicyclononane.

Most preferably, the catalyst is selected from one or more of the following:—LiOH, NaOH, KOH, RbOH, CsOH, Li(OR$^1$), Na(OR$^1$), K(OR$^1$), Rb(OR$^1$), Cs(OR$^1$), where R$^1$ is a methyl group; diazabicycloundecene and diazabicyclononane.

Preferred catalysts include Group I and Group II basic metal salts, for example lithium, sodium, potassium, rubidium, caesium, francium, beryllium, magnesium, calcium, strontium, barium or radium salts. Particularly preferred are lithium, sodium, potassium, rubidium, caesium or francium (i.e. Group I metal) salts.

In preferred embodiments of the present invention the catalyst comprises Group I methoxides or hydroxides, for example sodium methoxide, lithium methoxide, potassium methoxide, sodium hydroxide, lithium hydroxide or potassium hydroxide.

In particularly preferred embodiments the catalyst is a Group I or Group II methoxide, preferably a Group I methoxide. Group I methoxides, in particular lithium methoxide, has been shown by the inventors to be particularly advantageous since the catalyst is not inactivated as rapidly as other catalysts, and therefore may be used in a continuous process (in addition to batch reactions).

In embodiments, the $C_3$-$C_{12}$ methacrylate ester will be present in the organic phase removed in step c) of the present invention and the invention will include transesterifying the $C_3$-$C_{12}$ methacrylate ester. The transesterification of step d) may take place at the same time as or after the removal of the organic phase in step c).

In embodiments, the transesterification reaction takes place in conditions where the mol % water with respect to the catalyst is less than or equal to 500%, 400%, 300%, 200% or 100%. Preferably, the mol % water with respect to the catalyst is less than or equal to 90%, 80%, 70% or 60%. More preferably the mol % water with respect to the catalyst is less than or equal to 50%, 40%, 30%, 35%, 20%, 10%, 5%, 4%, 3%, 2% or 1%. Preferably the transesterification reaction takes place in the absence of water.

The inventors of the present invention have surprisingly shown that when water present during the transesterification reaction is reduced, conversion of $C_3$-$C_{12}$ methacrylate ester, particularly butyl methacrylate, to methyl methacrylate is increased. Therefore, in preferred embodiments of the invention, further purification (or drying) of the organic phase will take place before the transesterification of step d) to reduce the water (in the form of aqueous fermentation media, for example) present during the transesterification reaction.

Therefore, in embodiments, the process comprises a step of purifying (or drying) the organic phase, optionally prior to the transesterification of step d). Optionally, the purifying or drying is achieved by distillation.

In embodiments of the present invention, the process will further comprise e) purifying the MMA from a medium in which the transesterification reaction takes place. Such purification may be achieved by distillation, for example.

Fermentation and Fermentation Medium

In the present invention, microorganisms are provided in a fermentation medium under conditions which said microorganism will produce a $C_3$-$C_{12}$ methacrylate ester.

In embodiments, the present invention comprises culturing a microorganism in said fermentation medium. Culturing or cultivation suitably requires a carbon based feedstock upon which the microorganism may derive energy and grow. Preferably, therefore, the microorganism/s are cultured on a carbon based feedstock.

The fermentation medium may be a surrounding medium which surrounds the microorganism/s. Preferably a carbon based feedstock is present in the medium, optionally dissolved or suspended in the medium, bubbled through the medium and/or mixed with the medium. Preferably, therefore, the medium comprises the microorganism/s and the carbon based feedstock together with any buffers and salts.

The fermentation medium may be any commercially available medium suitable for the needs of the microorganism. The fermentation medium suitably contains a carbon based feedstock and a nitrogen source, as well as additional compounds required for growth of the microorganism/s and/or the formation of $C_3$-$C_{12}$ methacrylate ester.

Examples of suitable carbon based feedstocks known in the art include glucose, maltose, maltodextrins, sucrose, hydrolysed starch, starch, lignin, aromatics, syngas or its components, methane, ethane, propane, butane, molasses and oils. Preferably the carbon based feedstock is derived from biomass. Mixtures may also be used, as well as wastes, such as municipal waste, food waste and lignocellulosic wastes from food processing, forestry or agriculture.

Examples of suitable nitrogen sources known in the art include soy bean meal, corn steep liquor, yeast extract, ammonia, ammonium salts, nitrate salts, urea, nitrogen gas or other nitrogenous sources.

Examples of additional compounds which may be required for growth of the microorganism/s (and therefore may be present in the fermentation medium) include antibiotics, antifungals, anti-oxidants, buffers, phosphate, sulphate, magnesium salts, trace elements and/or vitamins.

Additional compounds required for growth of the microorganism/s and/or for the production of $C_3$-$C_{12}$ methacrylate ester, like phosphate, sulphate or trace elements, may be added in amounts that may vary between different classes of microorganisms, i.e. between fungi, yeasts and bacteria. In addition, the amount of additional compound to be added may be determined by what pathways are used to form the $C_3$-$C_{12}$ methacrylate ester.

The amount of carbon based feedstock and nitrogen source to be added to the medium may vary depending on the needs of the microorganism/s and/or the length of the culturing of the microorganisms. The ratio of the carbon based feedstock to the nitrogen source in the culture medium may vary considerably.

Typically, the amount of each fermentation medium component necessary for growth of a microorganism is determined by measuring the growth yield on the nutrient and further assessed in relation to the amount of carbon based feedstock used in the culturing process, since the amount of biomass formed will be primarily determined by the amount of carbon based feedstock used, and the nutrient limitations imposed during any feeding regime.

In embodiments where the carbon based feedstock is derived from biomass, the biomass preferably comprises a high amount of carbohydrates. Particularly preferable are carbohydrates which are sources of C5 or C6 sugars, carbon based gases, or aromatics, preferably C5 or C6 sugars, more preferably glucose, such as, but not limited to starch, lignin, cellulose, glycogen, arabinoxylan, chitin or pectin.

Alternatively, the biomass may comprise a high amount of fats, particularly preferable are fats or oils which are sources of glycerol and fatty acids, specifically triglycerides. Suitable triglycerides include any oil or fat which is readily available from a plant or animal source. Examples of such oils and fats include palm oil, linseed oil, rapeseed oil, lard, butter, herring oil, coconut oil, vegetable oil, sunflower oil, castor oil, soybean oil, olive oil, cocoa butter, ghee, blubber etc.

The biomass may be composed of one or more different biomass sources. Examples of suitable biomass sources include virgin wood, energy crops, agricultural residues, food waste, municipal waste and industrial waste or co-products.

Virgin wood biomass sources may includes but are not limited to wood chips, bark, brash, logs, sawdust, wood pellets or briquettes.

Energy crop biomass sources may include but are not limited to short rotation coppices or forestry, non-woody grasses such as miscanthus, hemp switchgrass, reeds or rye, agricultural crops such as sugar, starch or oil crops, or aquatic plants such as micro or macroalgae and weeds.

Agricultural residues may include but are not limited to husks, straw, corn stover, flour, grains, poultry litter, manure, slurry, syngas or silage.

Food wastes may include but are not limited to peel/skin, shells, husks, cores, pips/stones, inedible parts of animals or fish, pulp from juice and oil extraction, spent grains or hops from brewing, domestic kitchen waste, lard or oils or fats.

Industrial wastes may include but are not limited to untreated wood including pellets, treated wood, shale gases, wood composites including medium-density fibreboard (MDF)/oriented strand boards (OSB), wood laminates, paper pulp/shreddings/waste, textiles including fibre/yarn/effluent, or sewage sludge.

The microorganism may be cultured as a batch, a repeated batch, a fed-batch, a repeated fed-batch or a continuous cultivation process.

The culturing process is preferably performed on an industrial scale. An industrial scale process is understood to encompass a culturing process in one or more fermenters of a volume scale which is $\geq 0.01$ m$^3$, preferably $\geq 0.1$ m$^3$, preferably $\geq 0.5$ m$^3$, preferably $\leq 5$ m$^3$, preferably $\leq 10$ m$^3$, more preferably $\leq 25$ m$^3$, more preferably $\leq 50$ m$^3$, more preferably $\leq 100$ m$^3$, most preferably $\geq 200$ m$^3$.

In embodiments, the culturing is performed in a bioreactor. A bioreactor is generally understood to mean a container in which microorganisms are industrially cultured. Bioreactors can be of any size, number and form, and can include inlets for providing nutrients, additional compounds for growth, fresh medium, carbon based feedstocks, additives of gases, such as, but not limited to, air, nitrogen, oxygen or carbon dioxide. Bioreactors may also comprise outlets for removing volumes of the culture medium to collect the $C_3$-$C_{12}$ methacrylate ester from the fermentation medium. The bioreactor may also have an outlet for sampling of the culture.

The bioreactor can generally be configured to mix the fermentation medium, for example, by stirring, rocking, shaking, inverting, bubbling of gas through the culture etc. Alternatively, some continuous cultures do not require mixing, for example microreactor systems using a plug flow system. Bioreactors are common and well known in the art and examples may be found in standard texts, such as 'Biotechnology: A Textbook of Industrial Microbiology, Section Edition (1989) Authors: Wulf Cruegar and ANnelise Crueger, translated by Thomas D. Brock Sinauer Associates, Inc., Sunderland, MA.

The described and illustrated embodiments are to be considered as illustrative and not restrictive in character, it being understood that only the preferred embodiments have been shown and described and that all changes and modifications that come within the scope of the inventions as defined in the claims are desired to be protected.

It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," or "at least one," are used to preface a feature there is no intention to limit the claim to only one such feature unless specifically stated to the contrary in the claim.

BRIEF DESCRIPTION OF THE DRAWINGS

The present invention will now be further described with reference to the following figures which show.

DETAILED DESCRIPTION

Figure 1:
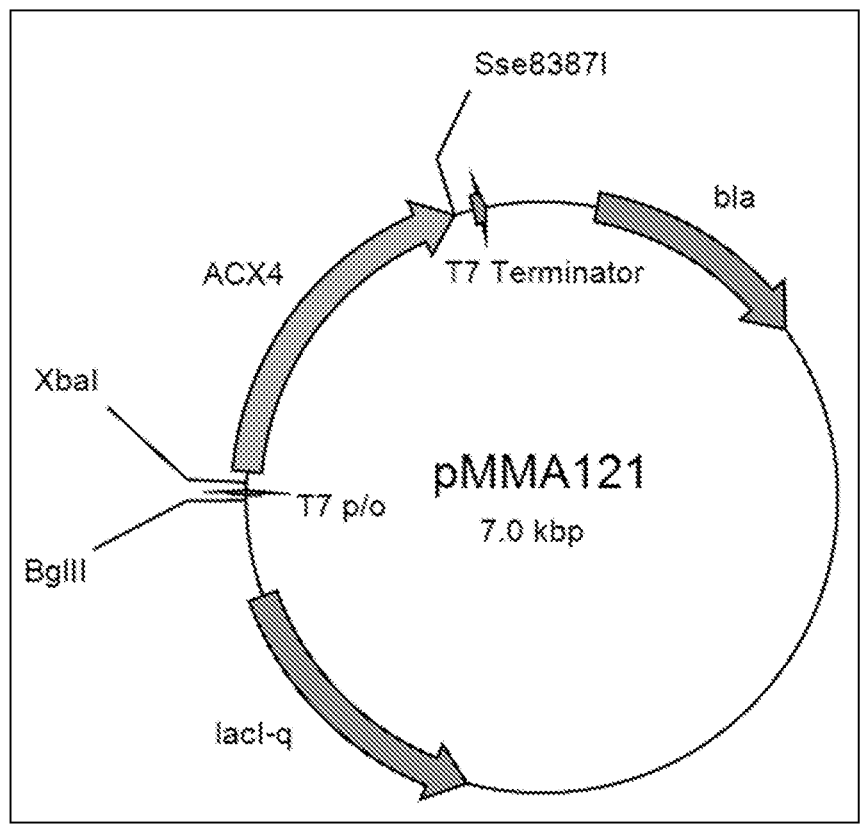
FIG. 1: The structure of plasmid pMMA121 for expression of the *Arabidopsis thaliana* ACX4 protein in *E. coli*.

The present inventors undertook extensive testing to determine how MMA might be efficiently produced by using microorganisms. In particular, though extensive experimentation, the present inventors have developed a process by which MMA can be produced via a step in which a $C_3$-$C_{12}$ methacrylate ester is produced by fermentation. The present inventors have surprisingly been able to develop such a process despite the toxicity of such $C_3$-$C_{12}$ methacrylate esters to microorganisms which was previously considered to make such a process unfeasible.

General Materials & Methods

Culture Growth and Maintenance
Microorganisms

*Escherichia coli* and *Saccharomyces cerevisiae* strains were stored in 16% glycerol stock solutions at −80° C. Working cultures were prepared on agar plates.

Luria Bertani (LB) and Agar Preparation

Luria Bertani high salt medium (Melford) (25 g/L) was used whenever LB medium is referred to. LB medium was prepared by dissolving peptone from casein digest (10 g), yeast extract (5 g) and sodium chloride (10 g) in 1 litre of water. The mixture was sterilised by autoclaving at 126° C. for 15 minutes, then left to cool to room temperature. Liquid LB medium was stored in a sealed sterile Duran bottle for up to one week at room temperature. LB agar plates were prepared using LB high salt medium (25 g/l) and agar (20 g/l). The LB and agar mixture was sterilised by autoclaving and allowed to cool in a 50° C. water bath prior to pouring, using aseptic techniques into sterile petri dishes. Plates were stored for up to two weeks at 4° C.

Yeast Extract-Peptone-Dextrose (YEPD) and Aqar Preparation

Yeast extract-Peptone-Dextrose (YEPD) medium and agar plates were prepared by dissolving yeast extract (3 g), malt extract (3 g), peptone from soybeans (5 g) and glucose (10 g) in distilled water (1 l). Agar (15 g) was added if preparing agar plates. The mixture was autoclaved at 126° C. for 15 minutes and then allowed to cool to 60° C. before pouring the plates using aseptic techniques into sterile petri dishes. Plates were stored for up to two weeks at 4° C. Liquid YEPD medium was stored for up to one week at room temperature.

MSX Broth Preparation

Minimal salts (MSX) medium was prepared in three parts; MSA, MSB and Vishniac Trace Elements. Vishniac trace elements solution (1 l) was prepared by combining EDTA disodium salt (50 g) with water (800 ml), dissolved by adding KOH pellets (2-3 at a time). Chemicals were then added in the following order; $ZnSO_4$ (2.2 g), $CaCl_2$ (5.54 g), $MnCl_2.4H_2O$ (5.06 g), $FeSO_4.7H_2O$ (5 g), $(NH_4)_6Mo_7O_{24}.4H_2O$ (1.1 g), $CuSO_4.5H_2O$ (1.57 g) and $CoCl_2.6H_2O$ (1.61 g). The solution was adjusted to pH 6 using KOH (1 M) then made up to 1 l using water. The solution was stored for up to six months at 4° C. MSA was prepared by dissolving $KH_2PO_4$ (6 g) and Vishniac trace elements (2 ml in water (660 ml). The solution was adjusted to pH 7 using KOH (1 M). The solution was then made up to 760 ml with water. MSB was prepared by dissolving $NH_4Cl$ (3 g) and $MgSO_4.7H_2O$ (0.4 g) in water (200 ml). A stock solution of glucose (12.5%) was also prepared by dissolving D-glucose (12.5 g) in water (100 ml). MSA, MSB and glucose (40 ml) were autoclaved at 126° C. separately for 15 minutes then combined aseptically once cooled, the final solution having a pH of 6.8. The solution was stored for up to one week at room temperature.

Cultivation of Microorganisms in Liquid Medium

General

From glycerol stock solutions, E. coli and S. cerevisiae were streaked onto sterile agar plates using four disposable inoculation loops. The inoculated plates was placed in an incubator overnight at 37 or 30° C. for E. coli and S. cerevisiae, respectively. An appropriate amount of sterile LB, YEPD or MSX medium (25 ml of medium in a 100 ml flask and 50 ml of medium in a 250 ml flask) was added to a sterile Erlenmeyer flask, fitted with a polyurethane foam bung and covered with aluminium foil, using aseptic techniques. To inoculate from an agar plate, a well isolated single colony was removed from the plate using a disposable inoculation loop. The colony was transferred to a pre-autoclaved flask containing the appropriate medium. The flask stopper was replaced and the flask incubated in an orbital incubator at 30 or 37° C., 200 rpm, for the respective microorganism. Once an $OD_{600}$ value of ≈0.8 was reached, an aliquot of inoculum was removed from the overnight culture using a sterile pipette and transferred to a pre-autoclaved flask. The type of flask and volumes required at this stage of cultivation was specific to each test and are stated in each relevant section in this chapter. This method was used to initially inoculate all cultures for growth and toxicity tests carried out throughout this thesis.

Specific growth rates of cultures were calculated in the exponential growth phase using the equation $\ln Nt/N0=\mu t$, where Nt is the arbitrary light scattering units at time t (h) and $\mu$ is the growth rate (h−1). Growth rates varied slightly dependent on type of growth medium and also between different tests, therefore all growth test results are expressed as a percentage value of the control run alongside that particular test.

Growth Inhibition Tests—Shake-Flask Cultures

Methacrylate ester toxicity tests were carried out in sterile 40 ml Teflon sealed glass vials, due to their volatility and ability to degrade the plastic well plates. To each vial the appropriate medium of LB or MSX medium was added for E. coli, and YEPD for S. cerevisiae, by aseptic technique. The medium was then inoculated with an overnight culture of E. coli or S. cerevisiae (100 µl). One vial was then left containing only these components as a control test, and to the remaining three vials was added the desired methacrylate ester. The four vials per methacrylate ester were then transferred to an orbital incubator set to 30 or 37° C., 250 rpm, for E. coli or S. cerevisiae, respectively. The aqueous medium phase was sampled every 30 minutes initially, and every 10 min once the cells entered the exponential growth phase, and again every 30 min once the stationary phase was reached, to produce a growth curve. Samples were taken through the Teflon-sealed lids using a sterile glass syringe and needle, and the OD600 values were recorded using a UV/Vis spectrophotometer, diluting samples to the appropriate detection range.

TABLE OF PRIMERS AND SEQUENCES

| REF | PRIMER SEQUENCE (5' to 3') | SEQ ID |
|---|---|---|
| BCKAD.F | GGCCTGTCATGAGTGATTACGAGCCG | 1 |
| BCKAD.R | CGGCCCTGCAGGTTCGCGGGAATCAGATGTGC | 2 |
| AAT.F | AGGAGATATACCATGAAAAGCTTTTCTGTACTC | 3 |
| AAT.R | AGCAGCCGGATCCCCTGCAGGACTAGTTTACTG GCTGGTGCTAC | 4 |
| ACX4.F | CACCAGCCAGTAAGCTAGCAAGGAGATATACCA TGGCTG | 5 |
| ACX4.R | TCCCCTGCAGGACTAGTTTACAGGCGAGAACGG GTAG | 6 |

Table of plasmids

| PLASMID REFERENCE | SOURCE | DESCRIPTION |
|---|---|---|
| pET16b(Sse) | This work | The pET16b expression vector with a modified Sse8387I restriction site. |
| pMMA121 | This work | The pET16b (Sse) expression vector containing the ACX4 gene from A. thaliana optimized for expression in pET16b (Sse) between its XbaI and Sse8387I restriction sites. |
| pWA008 | This work | The pET16b(Sse) expression vector containing the operon which encodes the BCKAD complex from P. aeruginosa PA01 strain inserted between its NcoI and Sse8387I restriction sites. |
| pAAT212 | This work | The pET(Sse) expression vector containing the AAT gene from Apple optimised for expression in pET16b (Sse) inserted between its NcoI and Sse8387I restriction sites |

-continued

Table of plasmids

| PLASMID REFERENCE | SOURCE | DESCRIPTION |
|---|---|---|
| pMMA133 | This work | The pAAT212 plasmid further containing the ACX4 gene from *A. thaliana* optimised for expression in the pET16b (Sse) vector inserted between the SpeI restriction site and the AAT gene. |
| pMMA134 | This work | The pMMA133 and the pWA008 plasmids ligated together and containing the ACX4 gene from *A. thaliana* optimised for expression in the pET16b (Sse) vector, the AAT gene from Apple optimised for expression in the pET16b (Sse) vector, and the BCKAD complex from *P. aeruginosa* PA01 strain inserted between the XbaI and Sse8387I restriction sites. |

Analytical Methods
Biomass Concentration

Optical density (OD) measurements were made at 600 nm with an Agilent 8453 spectrophotometer using polystyrene cuvettes (10 mm path length). Samples (1 ml) to be analysed were transferred to cuvettes and the OD measured. When the reading was outside of a range from 0-0.8, samples were diluted 1 in 10 in $dH_2O$ until they were within the specified range.

Gas Chromatography

The samples from the BMA/MMA extraction experiments were analysed using gas chromatography under the following operating conditions:

| Column | Agilent HP-5MS (325° C. max) |
|---|---|
| Column dimensions | 30 m × 0.25 mm × 0.25 μm nominal |
| Gas | Helium |
| He flow rate | 1.00 ml min$^{-1}$ |
| Detector | FID |
| Oven set point | 55° C. |

| Oven Ramp | ° C./min | Next ° C. | Hold min | Run time |
|---|---|---|---|---|
| Initial | | 55 | 3.5 | 3.5 |
| Ramp1 | 30 | 180 | 1 | 8.67 |

The samples from the transesterification experiments were analysed using gas chromatography under the following operating conditions:

| Column | RTX-1701 (from Thames Restek) |
|---|---|
| Column dimensions | 62 m × 0.32 mm × 1.0 μm nominal |
| Gas | Hydrogen |
| $H_2$ flow rate | 2.01 ml min$^{-1}$ |
| Detector | FID |
| Oven set point | 60° C. |

| Oven Ramp | ° C./min | Next ° C. | Hold min | Run time |
|---|---|---|---|---|
| Initial | | 60 | 10 | 10 |
| Ramp 1 | 10 | 180 | 2 | 24 |
| Ramp 2 | 20 | 220 | 6 | 32 |

EXAMPLES

Toxicity of Higher Methacrylate Esters to *E. coli* and *S. cerevisiae*

The present inventors investigated the toxicity of $C_3$-$C_{12}$ methacrylate esters to mircroorganisms, in particular the *E. coli* strain MG1655 and the *S. cerevisiae* strain DSM70449. In particular, the relative toxicities of methyl methacrylate (MMA), isopropyl methacrylate (iPMA) and butyl methacrylate (BMA) were investigated by growing *E. coli* MG1655 and *S. cerevisiae* DSM70449 in LB and YEPD medium respectively, in the presence of various concentrations of the methacrylate esters.

Final biomass concentrations were recorded after 72 hours and were used to calculate the inhibitory concentration ($IC_{50}$) for each ester. This is the concentration of ester that halves the maximum optical density ($MaxOD_{600}$) compared to growth in the absence of the ester (see Table 1).

TABLE 1

The calculated $IC_{50}$ values of methacrylate esters towards *E. coli* and *S. cerevisiae* grown in complex medium.

| | | $IC_{50}$ range (g/l) | |
|---|---|---|---|
| Methacrylate Ester | logP$_{o/w}$ | *S. cerevisiae* | *E. coli* |
| MMA | 0.95 | 0.73-1.45 | 3.19-4.25 |
| iPMA | 1.81 | 0.66-0.99 | 1.18-1.77 |
| BMA | 2.57 | 0.04-0.07 | 0.07-0.11 |

The toxicities of MMA, iPMA and BMA towards *E. coli* were also determined when the cells were grown in MSX medium. Final biomass concentrations were used to calculate the inhibitory concentration ($IC_{50}$) for each ester (see Table 2).

TABLE 2

The calculated $IC_{50}$ values of methacrylate esters towards *E. coli* grown in MSX medium.

| Methacrylate Ester | logP$_{o/w}$ | $IC_{50}$ range (g/l) |
|---|---|---|
| MMA | 0.95 | 3.19-4.25 |
| iPMA | 1.81 | 1.18-1.77 |
| BMA | 2.57 | 0.07-0.11 |

All the esters tested were toxic towards both *E. coli* and *S. cerevisiae* (Tables 1 and 2). However, significantly increased toxicity was shown in the presence of BMA compared to the shorter chain methacrylate esters, making the use of fermentation to produce this ester difficult, due to the toxicity exhibited towards the microorganism.

Production of butyl methacrylate from 2-ketoisovalerate by recombinant *Escherichia coli*

The present inventors then undertook experimentation to determine whether $C_3$-$C_{12}$ methacrylate esters, for example butyl methacrylate, could be produced by microorganisms such as *E. coli*.

The ACX4 gene from *Arabadopsis thaliana* was codon optimized for *E. coli*, synthesised and cloned into pET16b (Sse) vector. This gene was digested with Nhe1/Sse8387I and ligated in pET16b (Sse) digested with Xba1/Sse8387I. The resultant plasmid, pMMA121 (see FIG. 1), was introduced into *E. coli* BL21(DE3), and the recombinant *E. coli* (BL21(DE3)/pMMA121) was cultured as follows.

BL(DE3/)pET16b (vector control) or BL21(DE3)/pMMA121 was inoculated in LB medium supplemented with ampicillin (0.1 mg/ml) and grown overnight in a test tube at 37° C. An aliquot of an overnight culture was transferred to 100 ml of the same medium in a flask and shaken at 37° C. for 2-3 hours. IPTG (final 1 mM) was added to the flask and the culture was incubated with shaking at 20° C. overnight.

Cells were harvested by centrifugation and suspended in 0.1 M sodium phosphate buffer (pH 7.0), then disrupted by sonication. The disrupted E. coli cells were centrifuged to supernatant and pellet fractions, and both the vector control and the cells containing pMMA121 were analysed for ACO (acyl-CoA oxidase) activity (see FIG. 2) and expression for ACX4 protein by SDS-PAGE (see FIG. 3).

Figure 2:
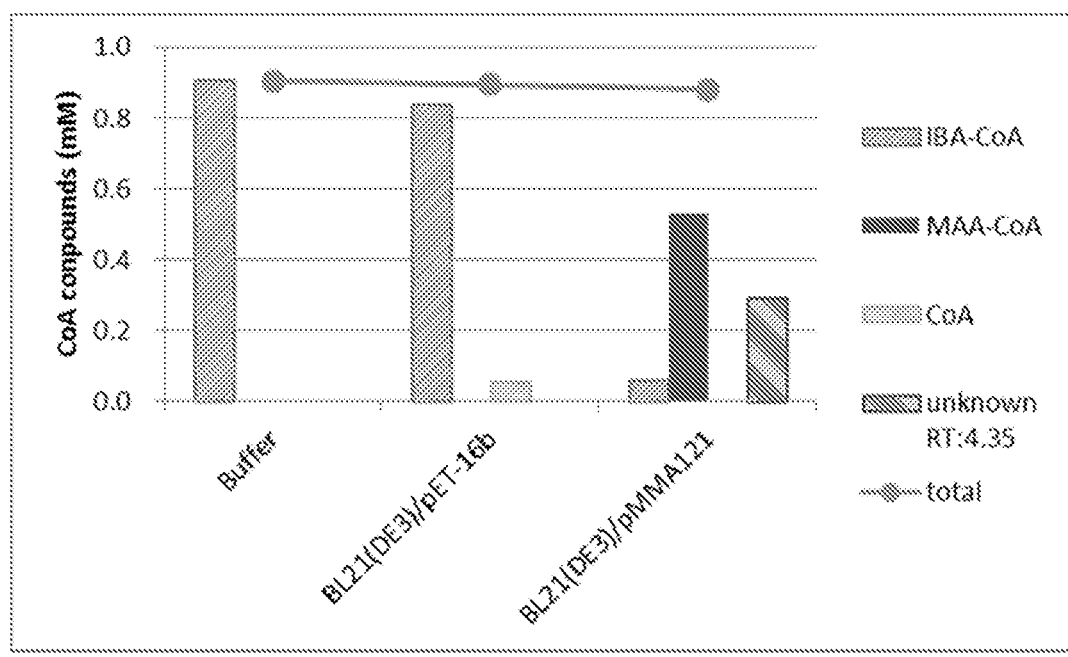
FIG. 2: The production of methacrylyl-CoA from isobutyryl-CoA using the *Arabidopsis thaliana* ACX4 protein produced from recombinant *E. coli*.
Figure 3:
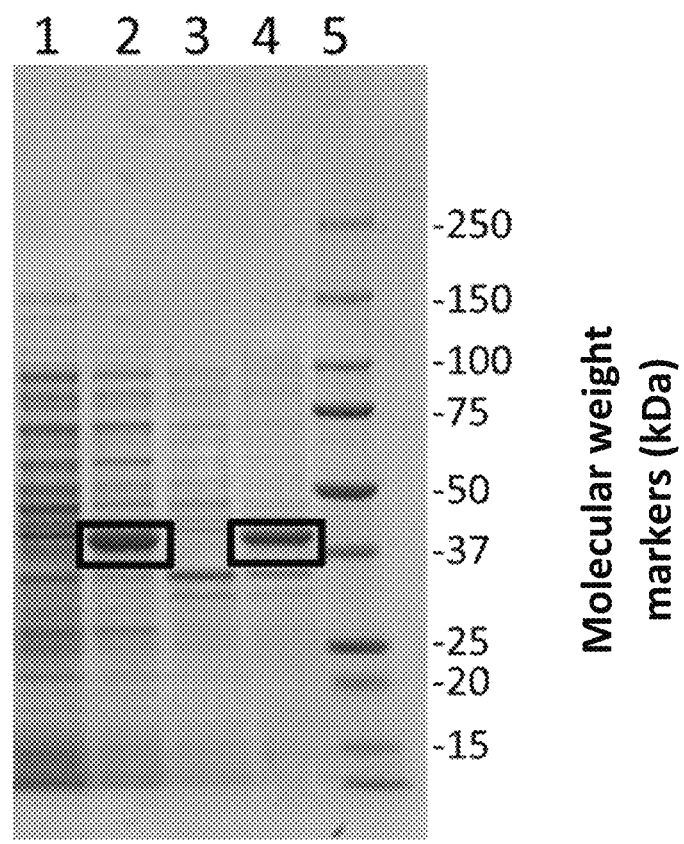
FIG. 3: SDS-PAGE analysis of fractions of the recombinant *E. coli* containing the *Arabidopsis thaliana* ACX4 protein.

FIG. 2 shows the presence of only IBA-CoA in the buffer, the presence of IBA-CoA and a small amount of CoA in the sample containing cells comprising only the unaltered plasmid pET16b, and the presence of MAA-CoA, much less IBA-CoA and an unknown compound in the sample containing cells comprising the plasmid pMMA121. Therefore, a high ACO activity was detected in the supernatant fraction of BL21(DE3)/pMMA121 indicated by the production of methacrylyl CoA, showing that the 40 kDa protein detected by the SDS-PAGE of FIG. 3 is the ACX4 protein. The SDS-PAGE shows, at lane 1—BL21/pET16b (vector) SF (soluble fraction); lane 2—BL21/pMMA121 SF; lane 3—BL21/pET16b IF (insoluble fraction); lane 4—BL21/pMMA121 IF; and lane 5—molecular weight marker. Around 40 kDa, a band (highlighted by black boxes) was observed only in the BL21/pMMA121 lanes but not in the BL21/pET16b (vector) lanes.

Figure 4:
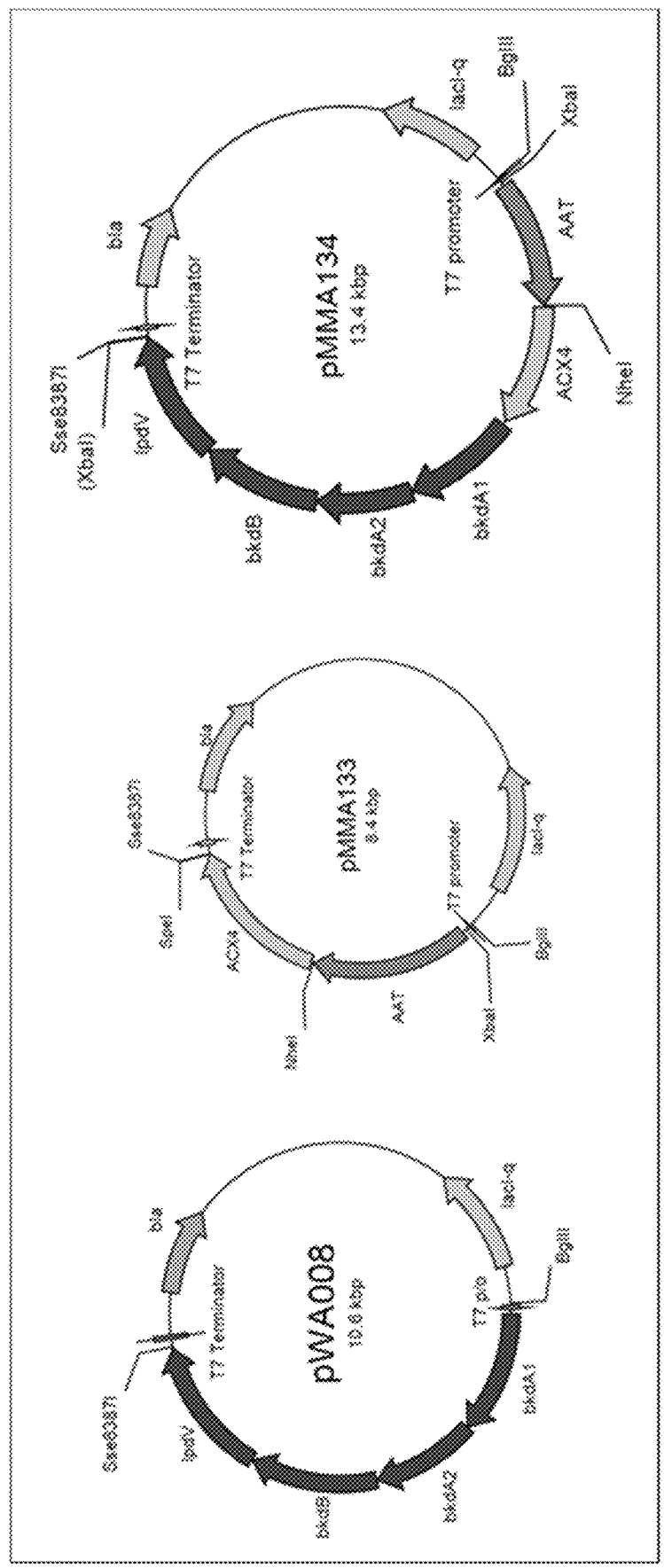
FIG. 4: The structure of plasmids pWA008, pMMA133 and pMMA134 for the expression of Apple AAT (MpAAT1), ACX4 from *Arabidopsis thaliana*, and bkdA1, bkdA2, bkdB and IpdV: BCKAD complex genes from *Pseudomonas aeruginosa* PA01 strain in recombinant *E. coli*.

BCKAD complex gene was cloned from Pseudomonas aeruginosa PA01 strain as follows. A DNA fragment containing an entire gene operon which encodes the BCKAD complex gene was obtained by PCR with primers BCKAD.F and BCKAD.R using the genomic DNA as a template. The obtained fragment was digested with restriction enzymes BspHI and Sse83871, and inserted into the vector pET16b (Sse) between Nco1/Sse83871 (BamH site of pET16b was converted to Sse83871 site). The resultant plasmid was named pWA008 (see FIG. 4).

A plasmid for expressing Apple AAT and A. thaliana ACX4 was constructed as follows. DNA fragments containing AAT or ACX4 gene was amplified by PCT with primers AAT.F and AAT.R or ACX4.F and ACX4.R using a plasmid containing codon-optimised AAT gene or pMMA121 as a template, respectively. pET(Sse) vector was digested with restriction enzymes NcoI and Sse83871 and joined with the DNA fragment containing AAT gene, by using In-Fusion HD Cloning Kit (Takara Bio). The resultant plasmid, pAAT212, was digested with restriction enzyme SpeI and joined with the DNA fragment containing ACX4 gene, by using In-Fusion HD Cloning Kit. The resultant plasmid, pMMA133, contained AAT and ACX4 genes with T7 promoter control (see FIG. 4).

A plasmid expressing BCKAD, AAT and ACX4 was constructed as follows. Plasmid pMMA133 was digested with restriction enzymes SpeI and Sse838771, and the linearised DNA fragment was obtained. Plasmid pWA008 was digested with restriction enzymes XbaI and Sse83871 and the 5.0 kb fragment containing BCKAD complex gene was isolated. Both fragments were ligated using DNA Ligation Kit 'Mighty Mix' (manufactured by Takara Bio Inc.). The resultant plasmid pMMA134 (FIG. 4) was introduced into E. coli BL21(DE3) for butyl methacrylate production experiments.

E. coli BL21(DE3)/pMMA134 was cultured in essentially the same manner as described above in relation to expression of ACX4. Cells were harvested by centrifuge, washed with 0.1 M sodium phosphate buffer (pH 7.0) and suspended in the same buffer to obtain a cell suspension. By using cell suspension, about 1 ml of a resting cell reaction solution was prepared in each vial, which contained 40 mM 2-ketoisovalerate (2-oxoisovalerate), 60 mM butanol, 0.05 M sodium phosphate buffer (pH 7.0) and cells ($OD_{650}$=12.5). The reactions were carried out at 30° C., 180 rpm for 3 to 44 hour, and 1 ml acetonitrile was added to the vials and mixed well to stop the reaction. After filtration using a syringe filter DISMIC/hole diameter 0.45 micron (manufactured by ADVANTEC), analysis was made by HPLC on ODS column. The HPLC conditions were as follows: Apparatus: Waters 2695, Column: CAPCELL PAK C18 UG120, 2.0 mml·C.×250 mm, Mobile phase: 0.1% phosphoric acid/65% methanol, Flow amount: 0.25 ml/min, Run rime: 12 min, Column temperature: 35° C. and Detection: UB 210 nm.

Figure 5:
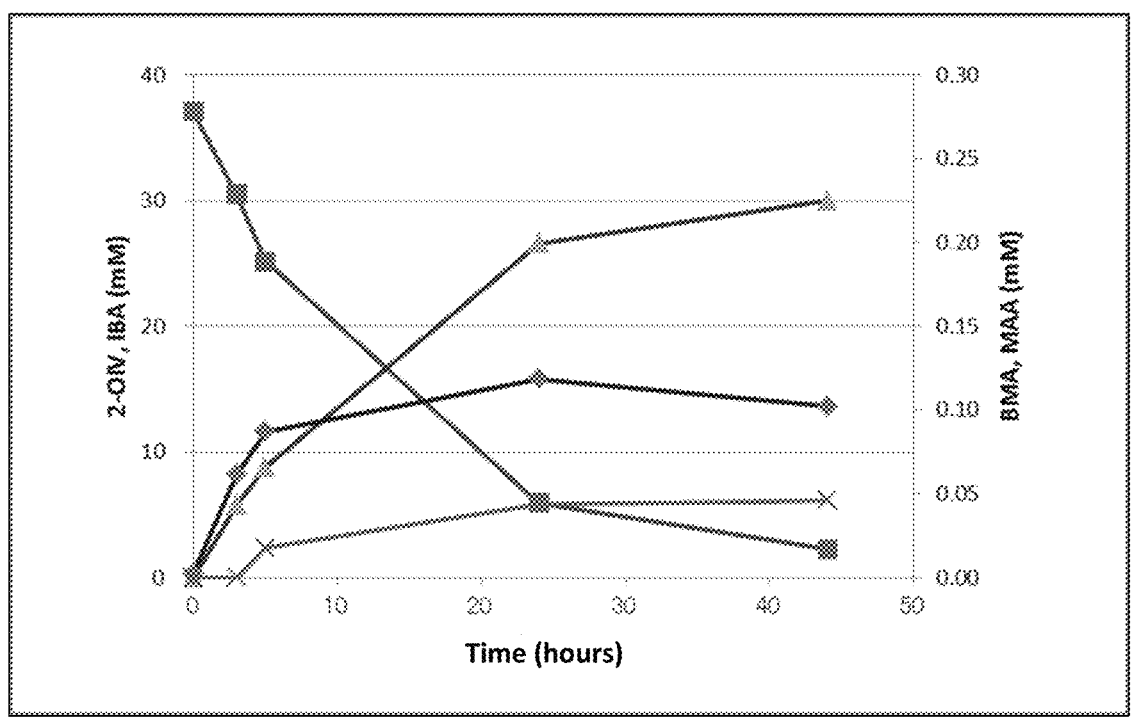
FIG. 5: The production of butyl methacrylate from 2-ketoisovalerate and butanol by HPLC analysis of a sample of the culture of recombinant *E. coli* production expressing plasmid pMMA134. ■, 2-ketoisovalerate (2-OIV); ▲, isobutyric acid (IBA); ♦, butyl methacrylate (BMA); and x, methacrylic acid (MAA).

FIG. 5 shows the concentration of the following chemicals over the time of the fermentation: ■, 2-ketoisovalerate (2-OIV); ▲, isobutyric acid (IBA); ♦, butyl methacrylate (BMA); and x, methacrylic acid (MAA). As the concentration of the feedstock of 2-ketoisovalerate (2-oxoisovalerate) falls, the production of the intermediate in the pathway isobutyric acid, increases, as does the production of the final ester product butyl methacrylate.

This example demonstrates viable in vivo production of a $C_3$-$C_{12}$ methacrylate ester, in particular butyl methacrylate, from the biochemical intermediate 2-ketoisovalerate (2-oxoisovalerate) which is produced directly from glucose, and the reagent butanol which is a common industrial feedstock. The production of butyl methacrylate is demonstrated at industrially applicable levels by culturing of recombinant E. coli cells expressing the BCKAD operon to convert 2-ketoisovalerate into isobutyryl CoA, ACX4 to convert isobutyryl CoA into methacrylyl CoA, and AAT to convert methacrylyl CoA into butyl methacrylate by reaction with butanol.

Extraction of BMA into Organic Solvents

Following the above investigation which demonstrated the production of butyl methacrylate from 2-ketoisovalerate by recombinant Escherichia coli, the present inventors undertook significant experimentation to investigate the extraction of $C_3$-$C_{12}$ methacrylate ester, for example BMA, from fermentation media.

In brief, five shake flask cultures were grown containing a variant E. coli strain similar to that used in the example above demonstrating the production of butyl methacrylate from 2-ketoisovalerate by recombinant Escherichia coli. Biomass was harvested from each flask and a separate biotransformation conducted. BMA and MMA levels in dodecane following solvent extraction was quantified by gas chromatography flame ionization detector (GC-FID).

In a 1 l baffled shake flask, a starter culture of 200 ml LB medium containing 200 pg/ml ampicillin was grown for 16.33 hours. The culture was back diluted to $OD_{600}$ 0.2 into 5 1 l baffled shake flasks containing 300 ml fresh LB medium and left to grow at 30° C. and 250 rpm for 23.35 hours. The biomass was then harvested by centrifugation at 5000 rpm and 4° C. for 15 minutes. Each cell pellet was washed with 100 mM sodium phosphate (pH 6.7) and the centrifugation step was repeated. The biomass was resuspended in the required volume of biotransformation medium until an $OD_{600}$ of 25 was reached.

Biotransformation reactions were conducted in 5×250 ml sealed Schott bottles at 30° C. and 180 rpm for 24 hours. The conditions for each biotransformation are shown in Table 3 below.

TABLE 3

| Biotransformation conditions | | |
|---|---|---|
| Biotrans # | Substrate/external std added | Concentration of sodium phosphate buffer (pH 6.7) |
| 1 | 40 mM 2-ketoisovalerate 60 mM 1-butanol | 50 mM |
| 2 | 0.28 mM BMA (40 mg/l) | 100 mM |
| 3 | 0.40 mM MMA (40 mg/l) | 100 mM |
| 4 | 0.70 mM BMA (100 mg/l) | 100 mM |
| 5 | 1 mM MMA (100 mg/l) | 100 mM |

Samples were taken for GC-FID analysis at 5 hour and 24 hour time points. At each time point 5 ml sample was removed and transferred to a 15 ml falcon tube. Acetonitrile (5 ml) was added in addition to dodecane (1 ml). The mixture was vigorously shaken at >800 rpm for 10 minutes before centrifugation at 3900 rpm and 20° C. for 20 minutes. A 500 μl sample was taken from both the organic and aqueous phases, filtered through a 0.45 μm filter and placed in a crimped lid gas chromatography vial prior to injection.

Quantification of BMA and MMA levels in biotransformation samples was achieved by using external standard calibration cultures obtained by preparing volumetric stock solutions of BMA and MMA at known concentrations.

The results of the extraction experiments are shown in Table 4 below:

TABLE 4

| | | Mass balance and extraction efficiencies of MMA and BMA into dodecane. | | | | | | | |
|---|---|---|---|---|---|---|---|---|---|
| Biotrans # | Sample timepoint | Amount of MMA added at t = 0 mins | Amount of BMA added at t = 0 mins | Total BMA observed | Total MMA observed | Amount extracted into dodecane | | Amount remaining in aqueous | |
| | h | mg/l | mg/l | mg/l | mg/l | mg/l | % | mg/l | % |
| 1 | 5 | — | — | 138 | — | 54.1 | 39.2 | 83.9 | 60.8 |
| | 24 | — | — | 102.4 | — | 47.5 | 46.4 | 54.9 | 53.6 |
| 2 | 5 | — | 40 | 37.1 | — | 11.1 | 29.9 | 26.0 | 70 |
| | 24 | — | 40 | 26.3 | — | 6.0 | 22.8 | 20.3 | 77.2 |
| 3 | 5 | 40 | — | — | 41.7 | 3.2 | 7.7 | 38.5 | 92.3 |
| | 24 | 40 | — | — | 28.9 | 3.4 | 11.8 | 25.5 | 88.2 |
| 4 | 5 | — | 100 | 72.8 | — | 26.5 | 36.4 | 46.3 | 63.6 |
| | 24 | — | 100 | 52.3 | — | 20.3 | 38.8 | 32.0 | 61.2 |
| 5 | 5 | 100 | — | — | 81.0 | 7.8 | 9.6 | 73.2 | 90.4 |
| | 24 | 100 | — | — | 49.3 | 6.4 | 13.0 | 42.9 | 87.0 |

The inventors demonstrated that the extraction efficiency of BMA into dodecane is consistently higher compared to MMA. For example, comparison of biotransformations 2 and 3 indicated a 2.7× higher extraction efficiency of BMA compared to MMA, and comparison of biotransformations 4 and 5 indicated a 3.3× higher extraction efficiency of BMA compared to MMA. Across all samples, the average amount of BMA extraction into dodecane was around 35.6% compared to 10.5% MMA.

Production of MMA from BMA by Transesterification

In the process of the present invention, BMA obtained via fermentation is transesterified to produce MMA. The inventors undertook experimentation to determine how an effective transesterification process which can operate with high reaction conversion and selectivity could be developed.

Transesterification reactions often make use of a catalyst to drive the reaction. Such catalysts can be acid catalysts, base catalysts or biocatalysts for example. A number of homo and heterogeneous catalysts have been used to drive the transesterification of MMA into higher molecular weight methacrylates. However, the reverse reaction has not been investigated.

A number of transesterification experiments were carried out using n-BMA, methanol and a range of catalysts.

The transesterification experiments were carried out in three necked Schlenk flasks under an inert atmosphere of nitrogen. The reaction temperatures were determined by feeding a thermocouple into the reaction solution. In general a number of reaction samples were taken during the reaction. However, if the final experimental sample showed that no reaction had taken place then the earlier samples were not analysed.

The levels of conversion of BMA to MMA using titanium butoxide, zirconium butoxide, zirconium acetylacetonate, a heterogeneous alkyl metal complex (caesium on silica), Amberlyst 15-H (a sulphonic acid functionalised polysytrene resin) were low (between 0 and 20%). However, the level of conversion using sodium methoxide, lithium methoxide and lithium hydroxide was much higher, as outlined below.

Transesterification of n-BMA with Methanol and Sodium Methoxide n-BMA (1 mol, 142.20 g), MeOH (1 mol, 32.04 g), 4-hydroxy-TEMPO (0.1 g) and NaOMe (1.01 g, 18.7 mmol) were added to a three necked 250 ml Schlenk flask under nitrogen. One neck of the flask was stoppered, one neck was stoppered with a silicon bunge which was used to feed a thermocouple into the reaction solution and the third neck attached to a condenser. The temperature was initially kept at approximately 20° C. for an hour, and then raised every hour by approximately 10° C., until reflux at 88.2° C. was achieved. At each temperature point a sample was taken and analysed by gas chromatography.

Figure 6:
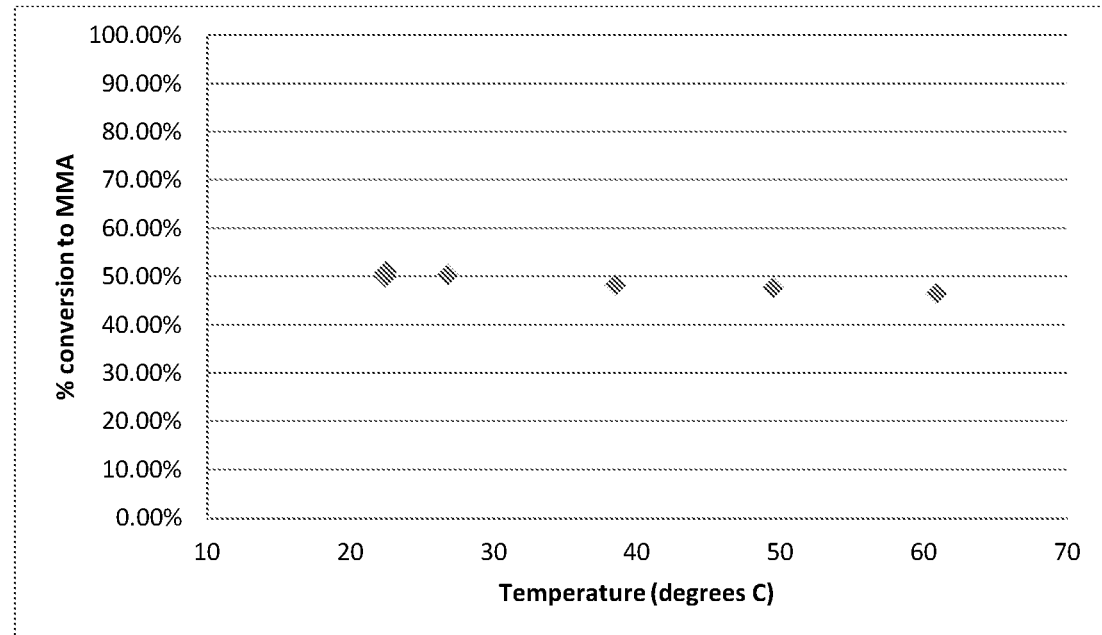
FIG. 6: Conversion of n-BMA to MMA versus reaction temperature using sodium methoxide as catalyst.

Using sodium methoxide as a catalyst resulted in good conversion of the n-BMA to MMA (around 50%; FIG. 6).

Transesterification of n-BMA with Methanol and Lithium Hydroxide n-BMA (1 mol, 142.20 g), MeOH (1 mol, 32.04 g), 4-hydroxy-TEMPO (0.1 g) and LiOH (1.01 g, 42 mmol) were added to a three necked 250 ml Schlenk flask under nitrogen. One neck of the flask was stoppered, one neck was stoppered with a silicon bung which was used to feed a thermocouple into the reaction solution and the third neck attached to a condenser. The temperature was initially kept at approximately 20° C. for an hour, and then raised every hour by approximately 10° C., until reflux at 88.2° C. was achieved. At each temperature point a sample was taken and analysed by gas chromatography.

Figure 7:
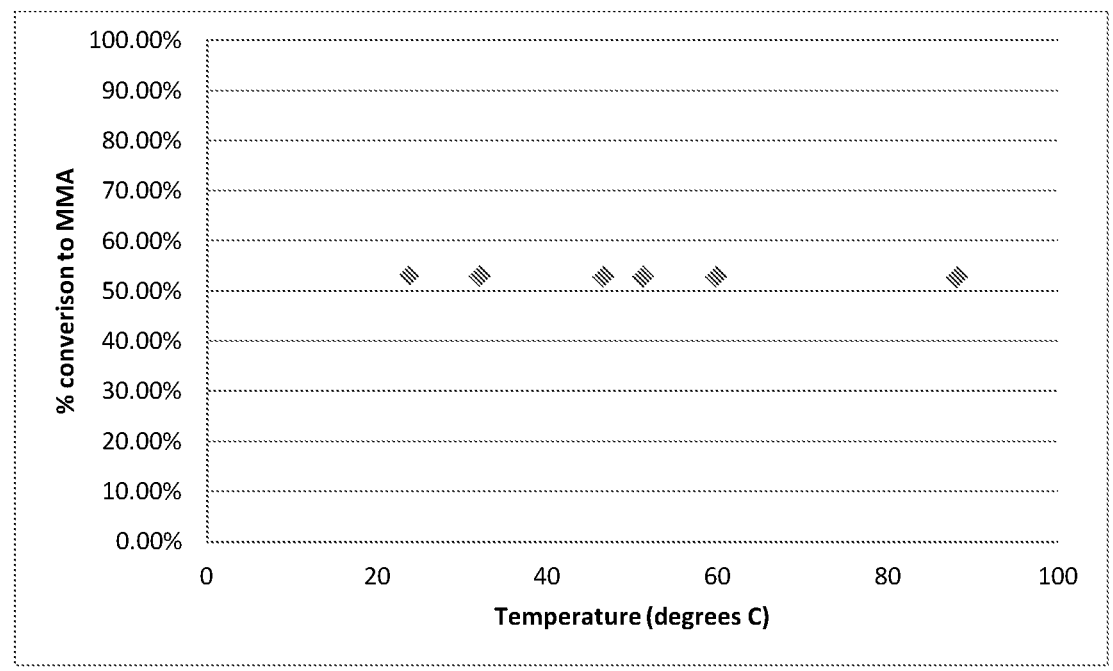
FIG. 7: Conversion of n-BMA to MMA versus reaction temperature using lithium hydroxide as catalyst.

Good conversion of n-BMA to MMA was achieved using lithium hydroxide as catalyst (between 5 and 60%; FIG. 7).

A repeat experiment was then carried out (using lithium hydroxide as catalyst) to determine the rate of the reaction at the reflux temperature of the reactants.

Figure 8:
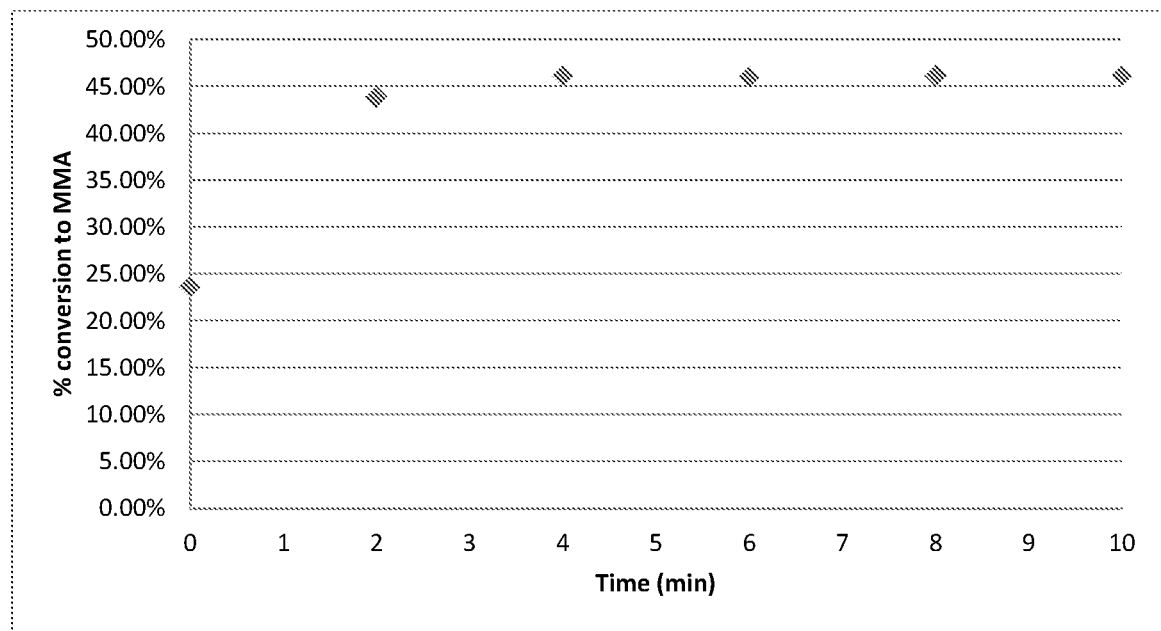
FIG. 8: Conversion of n-BMA to MMA versus time at a reaction temperature using lithium hydroxide as catalyst.

Lithium hydroxide (0.51 g, 21 mmol) was dissolved in methanol (32.43 g, 1 mol) by stirring in a sealed Schlenk flask. n-BMA (142.18 g, 1 mol) and 4-hydroxy-TEMPO (0.1 g) was added to a three necked 250 ml Schlenk flask under nitrogen and this mixture was heated to 88.2° C., with one neck stoppered, one bunged, and the other attached to a condenser. When reflux was reached and the temperature stabilised, the catalyst (lithium hydroxide) and MeOH solution was added to the reaction flask by syringe. A sample was taken every two minutes for the first ten minutes and every five minutes for an hour. The samples were then analysed by gas chromatography. As shown in FIG. 8, equilibrium ratios of n-BMA and MMA was achieved after heating for four minutes.

Transesterification of n-BMA with Methanol and Lithium Methoxide

Lithium methoxide (0.79 g, 20.9 mmol) was dissolved in methanol (32.04 g, 1.00 mol) by stirring in a sealed flask. A solution of nBMA (142.20 g, 1.00 mol) and 4-hydroxy-TEMPO (0.10 g) was heated under a nitrogen atmosphere (91° C.). When the temperature had stabilised, the catalyst and methanol solution was added and reflux achieved (88° C.). Samples were taken every two minutes for the first ten minutes and every half an hour for an hour. These samples were filtered through silica and analysed by gas chromatography.

Figure 9:
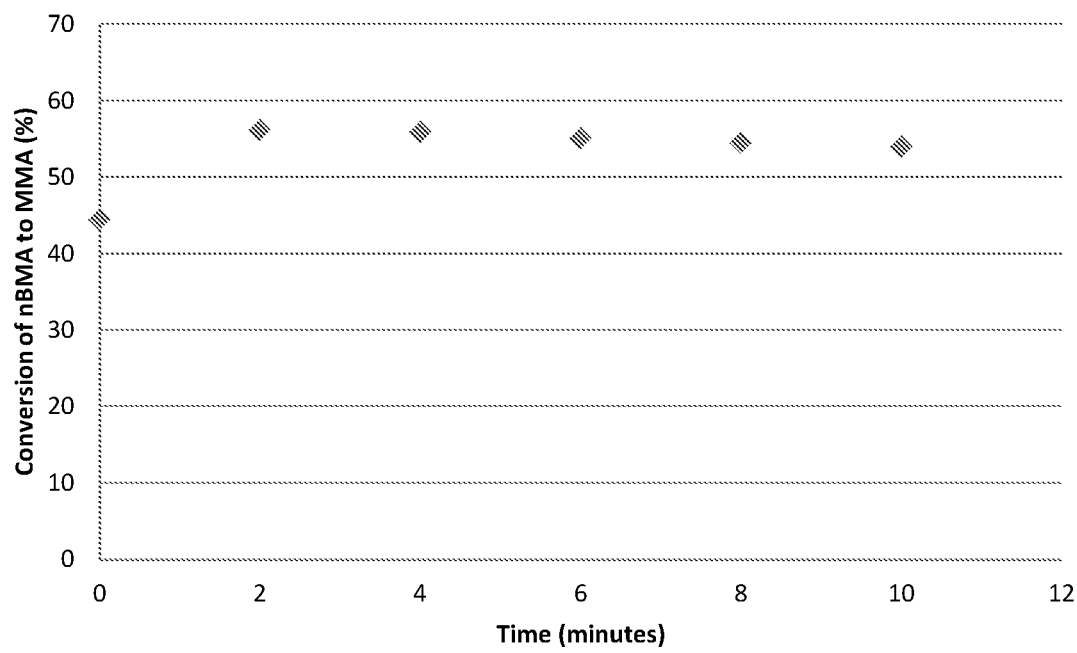
FIG. 9: Change in conversion of nBMA to MMA with time in a reaction catalysed by lithium methoxide.

A conversion of nBMA to MMA of 53±3% was achieved after four minutes (FIG. 9).

Comparing LiOH and LiOMe as Catalysts for the Transesterification of nBMA to MMA The degree of deactivation of two lithium catalysts, lithium hydroxide and lithium methoxide, was also investigated. This was to determine catalyst lifetimes.

This was investigated by running transesterification reactions of nBMA with methanol using LiOH and LiOMe catalysts. After an hour at reflux a further mole of nBMA and mole of methanol was added to the reaction, and the conversion to MMA was time monitored.

A solution of nBMA (142.20 g, 1.00 mol), methanol (32.04 g, 1.00 mol) and 4-hydroxy-TEMPO (0.10 g) was treated with a catalyst and heated to reflux (87° C.) under a nitrogen atmosphere. After an hour at reflux further nBMA (142.20 g, 1.00 mol) and methanol (32.04 g, 1.00 mol) was added to the reaction solution. Samples were taken every two minutes for the first ten minutes and every half an hour for an hour. These samples were filtered through silica and analysed by gas chromatography. LiOH (0.50 g, 20.9 mmol) and LiOMe (0.79 g, 20.9 mmol) catalysts were utilised.

Figure 10:
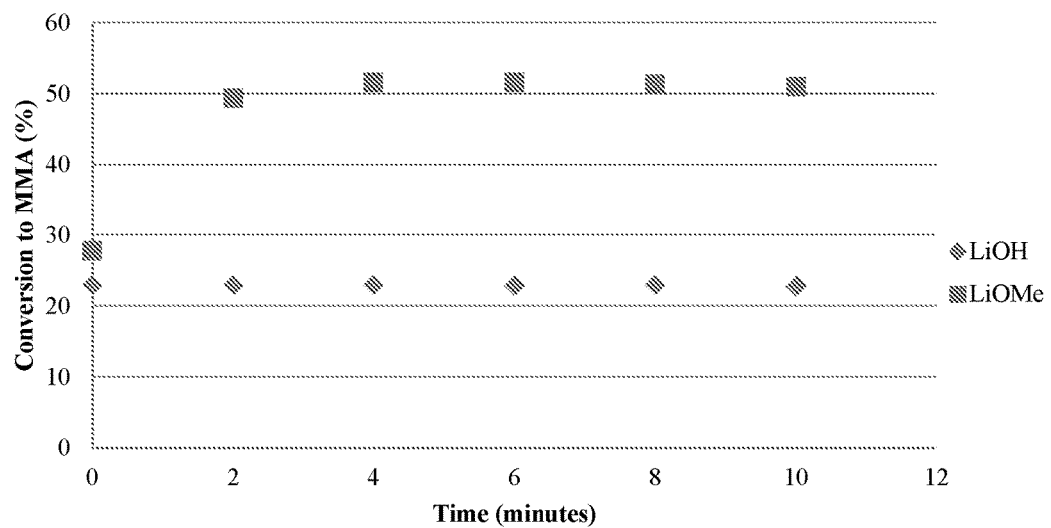
FIG. 10: Plot of conversion to MMA against time for the transesterification reaction of nBMA upon further addition of methanol and nBMA after an initial transesterification reaction catalysed by LiOH and LiOMe.

Upon the addition of additional nBMA and methanol to the transesterification reaction solution catalysed by LiOH no further increase in conversion to MMA was observed. This indicates that all the catalyst had been deactivated by the water formed in the first transesterification reaction so no further reaction could occur when fresh reactants were added (FIG. 10). However, with the LiOMe catalysed transesterification solution, when more reactants were added the conversion to MMA increased until equilibrium was reached (FIG. 10).

This data indicates that the use of LiOH as catalyst would require addition of fresh LiOH over time to maintain the reaction. However, LiOMe would not need to be added as frequently and therefore may be more suited to a continuous reaction. The inactivation of LiOH is likely to be due to the conversion of LiOH to LiMMA; LiOMe does not react with methanol to form water in situ and therefore is not deactivated as quickly.

Effect of Increasing the Amount of Water in the Transesterification Reaction

In the process of the present invention, the fermentation reaction takes place in an aqueous environment and so the $C_3$-$C_{12}$ methacrylate ester produced will be saturated with water. Surprisingly, however, water affects the transesterification reaction.

The consequence of the presence of water in the transesterification reaction is shown below in relation to the addition of increasing amounts of water to nBMA transesterification reactions with methanol. The reactions were run at reflux temperature and the conversion to MMA with time monitored. All percentages of water were determined as the moles of water with respect to the moles of LiOH (Table 5).

TABLE 5

Addition of water to transesterification reaction.

| Experiment number | Mass LiOH (g) | Mass Water (g) | Moles LiOH (mmol) | Moles Water (mmol) | mol % $H_2O$ with respect to LiOH |
|---|---|---|---|---|---|
| 1 | 0.50 | 0 | 20.9 | 0 | 0 |
| 2 | 0.50 | 0.13 | 20.9 | 7.18 | 34.09% |
| 3 | 0.50 | 0.53 | 20.9 | 29.5 | 140.29% |
| 4 | 0.50 | 2.01 | 20.9 | 112 | 522.98% |

Lithium hydroxide (0.50 g, 20.9 mmol) was dissolved in methanol (32.04 g, 1.00 mol) and water (0.13 g, 71.8 mmol) by stirring in a sealed flask. A solution of nBMA and 4-hydroxy-TEMPO (0.10 g) was heated to 90° C. under a nitrogen atmosphere. When the temperature had stabilised, the LiOH, methanol and water solution was added and a reflux temperature of 86° C. was observed. Samples were taken every two minutes for the first ten minutes and then after 30 minutes and 60 minutes. These samples were filtered through silica gel before being analysed by gas chromatography. This method was repeated with masses of water of 0.53 g and 2.01 g.

Figure 11:
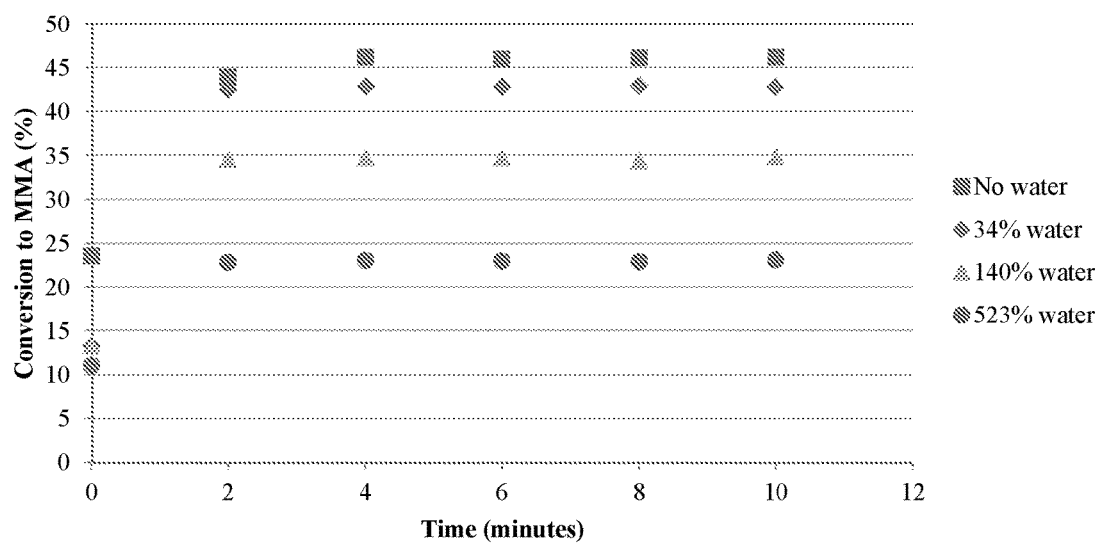
FIG. 11: Plot of conversion to MMA against time for the transesterification of nBMA with increasing water content.

From the results it is clear that increasing the water in the reaction decreases the conversion of nBMA to MMA (FIG. 11). These results indicate that although conversion of $C_3$-$C_{12}$ methacrylate ester to MMA can take place in the presence of water, it is advantageous if the presence of water is limited to improve conversion. Therefore, it may be advantageous to remove the $C_3$-$C_{12}$ methacrylate ester of the present invention from the aqueous environment prior to commencement of the transesterification reaction.

Biotransformation

Biotransformation experiments were carried out on a new strain of E. coli modified for methacrylate ester production to compare the biotransformation using different alcohols.

The cells were grown overnight in LB-Miller (Merck) plus ampicillin (200 µg/mL) in a baffled shake flask at 30° C. and at 250 rpm.

The resulting culture was centrifuged and the pellet resuspended to an OD of 50 with 0.1M sodium phosphate buffer (pH 7). An aliquot (15 mL) of this resuspended culture was placed into a 250 mL Schott bottle and 15 mL of 80 mM KIV (ketoisovalerate) stock solution was added. This provided an overall OD of 25 and a final concentration of 40 mM KIV and 0.05 M sodium phosphate buffer in 30 mL volume. Each alcohol was added neat to a final concentration of 5 mM. The biotransformation incubation was carried out in the Schott bottle at 30° C. and 250 rpm.

Samples were taken after 3.5 h incubation for GC-MS analysis to determine alkyl methacrylate ester levels.

Sampling was carried out by taking a 0.5 mL sample of the biotransformation broth adding 0.5 mL heptane and vortexing the mixture continuously for 5 minutes. The phases were then separated by microcentrifugation (14,800 rpm, 5 mins). A 0.2 mL sample of the resulting heptane extract was taken and placed into a GC vial (containing a 0.25 mL vial insert) and crimped. The sample was then subjected to GC-MS using an Agilent 6890 series GC with an Agilent 5973 mass selective detector (single quadrupole). The analytes were separated using an ZB-WAXPlus 30 m column, 250 µm internal diameter and 0.25 µm film thickness using helium carrier gas. Specific GC details are given in table 6 and the results are set out in table 7.

TABLE 6

GC Parameters

| | |
|---|---|
| Column Type | ZB-WAXPlus ™ |
| Column Length | 30 metres |
| Internal Diameter | 0.25 mm |
| Film Thickness | 0.25 µm |
| Carrier Gas | Helium |
| Flow Rate | 1 mL min$^{-1}$ |
| Injection Type | Split |
| Split Ratio | 50:1 |
| Injection Volume | 1 µL |
| Inlet Temperature | 250° C. |
| Pressure | 12.3 psi |

TABLE 7

Biotransformation with various Alcohols at 3.5 hours

| | Alkyl Methacrylate Ester Concentration 3.5 h |
|---|---|
| Methanol | 0.117 mM |
| Butanol | 1.031 mM |

TABLE 7-continued

Biotransformation with various Alcohols at 3.5 hours

| | Alkyl Methacrylate Ester Concentration 3.5 h |
|---|---|
| Pentanol | 2.122 mM |
| Hexanol | 0.756 mM |
| Heptanol | 1.460 mM |
| Octanol | 0.665 mM |

Conclusions

These studies indicate that $C_3$-$C_{12}$ methacrylate esters (in particular n-BMA) can be transesterified to produce MMA with particular high efficiency using group I and group II basic metal salts as catalysts and that the absence of water results in higher conversion efficiency. In addition, it has been shown that the production of higher esters proceeds at a faster rate than that of methyl methacrylate.

All of the features disclosed in this specification (including any accompanying claims, abstract and drawings), and/or all of the steps of any process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. The invention extends to any novel one, or any novel combination, of the features disclosed in this specification (including any accompanying claims, abstract and drawings), or to any novel one, or any novel combination, of the steps of any process so disclosed.

Furthermore, it will be appreciated that numerous modifications to the above described process may be made without departing from the scope of the invention as defined in the appended claims.

The invention claimed is:

1. A process for the production of methyl methacrylate (MMA), the process comprising the steps of:
   a) providing a microorganism that expresses one or more enzymes necessary to catalyse the production of $C_3$-$C_{12}$ methacrylate esters in a fermentation medium, under conditions which said microorganism will produce a $C_3$-$C_{12}$ methacrylate ester enzymatically;
   b) providing an organic phase in contact with the fermentation medium, said organic phase including $C_3$-$C_{12}$ methacrylate ester in a higher concentration than that in the fermentation medium;
   c) removing organic phase containing said $C_3$-$C_{12}$ methacrylate ester from contact with the fermentation medium; and
   d) transesterifying the removed $C_3$-$C_{12}$ methacrylate ester with methanol, optionally after separation from the organic phase, to produce methyl methacrylate, wherein the transesterification of step d) is non-enzymatic takes place in the presence of methanol and a base catalyst.

2. The process according to claim 1 wherein the methacrylate ester is selected from a $C_3$-$C_{12}$ alkyl, hydroxyalkyl, alkenyl, alkylaryl or alkenylaryl methacrylate ester.

3. The process according to claim 1, wherein the methacrylate ester is selected from n-propyl, isopropyl, isobutyl, n-butyl, t-butyl, isopentyl, hexyl, cyclohexyl, heptyl, octyl, 2-ethylhexyl, decyl, dodecyl, hydroxyethyl, hydroxypropyl, isobornyl, allyl or cinnamyl methacrylate.

4. The process according to claim 1, where the microorganism comprises E. coli, Corynebacterium glutamicum, Pseudomonas fluorescens or Pseudomonas putida.

5. The process according to claim 4, wherein the microorganism is genetically modified to produce more $C_3$-$C_{12}$ methacrylate ester than a wild-type microorganism.

6. The process according to claim 1, wherein the microorganism expresses one or more enzymes which can convert isobutyryl-CoA to methacrylyl-CoA.

7. The process according to claim 1, wherein the microorganism expresses one or more enzymes which can convert methacrylyl-CoA to a $C_3$-$C_{12}$ methacrylate ester.

8. The process according to claim 1, wherein the microorganism expresses an oxidase, dehydrogenase or oxidoreductase enzyme and an alcohol acyltransferase enzyme.

9. The process according to claim 8, wherein the oxidase is an acyl CoA oxidase.

10. The process according to claim 8, wherein the oxidase is acyl-coenzyme A oxidase 4 (ACX 4) from Arabidopsis thaliana.

11. The process according to claim 1, wherein the microorganism expresses one or more enzymes which can convert 2-ketoisovaleric acid to isobutyryl-CoA.

12. The process according to claim 11, wherein the enzyme comprises an oxidoreductase enzyme.

13. The process according to claim 12, wherein the oxidoreductase enzyme is a branched chain keto acid dehydrogenase enzyme complex that comprises branched chain keto acid dehydrogenase (BCKD) from *P. putida*, BCKD from *Bacillus subtilis*, BCKD from *P. aeuruginosa*, BCKD from *A. thaliana*, BCKD from *Streptomyces coelicolor* or BCKD from *Thermus thermophiles*.

14. The process of claim 1, wherein the catalyst is selected from metal oxide, hydroxide, carbonate, acetate (ethanoate), oxalate, alkoxide, hydrogencarbonate, a quaternary ammonium compound of one of the above, an alkyl or phenyl amine, diazabicycloundecene and diazabicyclononane.

15. The process of claim 1, wherein the catalyst is selected from one or more of the following: LiOH, NaOH, KOH, $Mg(OH)_2$, $Ca(OH)_2$, $Ba(OH)_2$, CsOH, $Sr(OH)_2$, RbOH, $NH_4OH$, $Li_2CO_3$, $Na_2CO_3$, $K_2CO_3$, $Rb_2CO_3$, $Cs_2CO_3$, $MgCO_3$, $CaCO_3$, $SrCO_3$, $BaCO_3$, $(NH_4)_2CO_3$, $LiHCO_3$, $NaHCO_3$, $KHCO_3$, $RbHCO_3$, $CsHCO_3$, $Mg(HCO_3)_2$, $Ca(HCO_3)_2$, $Sr(HCO_3)_2$, $Ba(HCO_3)_2$, $NH_4HCO_3$, $Li_2O$, $Na_2O$, $K_2O$, $Rb_2O$, $Cs_2O$, MgO, CaO, SrO, BaO, $Li(OR^1)$, $Na(OR^1)$, $K(OR^1)$, $Rb(OR^1)$, $Cs(OR^1)$, $Mg(OR^1)_2$, $Ca(OR^1)_2$, $Sr(OR^1)_2$, $Ba(OR^1)_2$, $NH4(OR^1)$ where $R^1$ is any C1 to C6 branched, unbranched or cyclic alkyl group, being optionally substituted with one or more functional groups; $NH_4(R^2CO_2)$, $Li(R^2CO_2)$, $Na(R^2CO_2)$, $K_2(R^2CO_2)$, $Rb(R^2CO_2)$, $Cs(R^2CO_2)$, $Mg(R^2CO_2)_2$, $Ca(R^2CO_2)_2$, $Sr(R^2CO_2)_2$ or $Ba(R^2CO_2)_2$, where $R^2CO_2$ is acetate; $(NH_4)_2(CO_2R^3CO_2)$, $Li_2(CO_2R^3CO_2)$, $Na_2(CO_2R^3CO_2)$, $K_2(CO_2R^3CO_2)$, $Rb_2(CO_2R^3CO_2)$, $Cs_2(CO_2R^3CO_2)$, $Mg(CO_2R^3CO_2)$, $Ca(CO_2R^3CO_2)$, $Sr(CO_2R^3CO_2)$, $Ba(CO_2R^3CO_2)$, $(NH_4)_2(CO_2R^3CO_2)$, where $CO_2R^3CO_2$ is oxalate; ;
methylamine, ethylamine, propylamine, butylamine, pentylamine, hexylamine, cyclohexylamine, aniline;
$R_4NOH$ where R is methyl, ethyl propyl, butyl;
diazabicycloundecene and diazabicyclononane.

16. The process according to claim 1, wherein the catalyst is selected from a Group I or Group II metal salt.

17. The process of claim 1, wherein the catalyst is selected from Group I or Group II metal oxide, hydroxide, carbonate, acetate, oxalate, alkoxide and hydrogencarbonate.

18. The process according to claim 1, wherein the catalyst is a Group I metal salt.

19. The process according to claim 1, wherein the catalyst is a Group I methoxide.

20. The process according to claim 1, wherein the catalyst is a homogeneous catalyst.

21. The process according to claim 1, wherein the catalyst is selected from the group consisting of sodium methoxide, lithium methoxide, potassium methoxide, sodium hydroxide, lithium hydroxide, potassium hydroxide and mixtures thereof.

22. The process according to claim 1, wherein the transesterification of step d) takes place in conditions where the mol % water with respect to a catalyst is less than or equal to 50%.

23. The process of claim 1, further comprising a step of drying the organic phase wherein the step is carried out prior to the transesterification of step d).

24. The process according to claim 1, wherein the transesterification of step d) takes place in the absence of water.

25. The process according to claim 1, wherein the titre of $C_3$-$C_{12}$ methacrylate ester in the fermentation medium is 220 mg/l.

26. The process according to claim 1, wherein the organic phase provided in step b) is provided by the $C_3$-$C_{12}$ methacrylate ester produced by the microorganism.

27. The process according to claim 1, wherein the organic phase provided in step b) comprises an external organic solvent in contact with the fermentation medium.

28. The process according to claim 27, wherein the organic solvent is biocompatible.

29. The process according to claim 27, wherein the organic solvent has a logarithm of octanol/water partition coefficient ($logP_{o/w}$) value of greater than or equal to 3.0.

30. The process according to claim 27, wherein the solvent is selected from the group consisting of tributyrin, isopropylbenzene, n-propylbenzene, cycloheptane, hexane, heptane, cyclooctane, isooctane, 1,4-diisopropylbenzene, octane, nonane, decane, undecane, dodecane and mixtures thereof.

31. The process according to claim 1, further comprising purifying the $C_3$-$C_{12}$ methacrylate ester in said organic phase.

32. The process according to claim 12, wherein the oxidoreductase enzyme is a branched chain keto acid dehydrogenase (BCKD) enzyme complex.

33. The process according to claim 1, wherein the microorganism is genetically modified and expresses an exogenous gene encoding an acyl CoA oxidase.

\* \* \* \* \*